United States Patent
He et al.

(10) Patent No.: US 10,837,056 B2
(45) Date of Patent: *Nov. 17, 2020

(54) CONFORMATIONAL PROBES AND METHODS FOR SEQUENCING NUCLEIC ACIDS

(71) Applicant: Illumina, Inc., San Diego, CA (US)

(72) Inventors: Molly He, San Diego, CA (US); Cheng-Yao Chen, San Diego, CA (US); Eric Kool, Stanford, CA (US); Mostafa Ronaghi, San Diego, CA (US); Michael Previte, Carlsbad, CA (US); Rigo Pantoja, Carlsbad, CA (US)

(73) Assignee: Illumina, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/352,731

(22) Filed: Mar. 13, 2019

(65) Prior Publication Data

US 2019/0376136 A1 Dec. 12, 2019

Related U.S. Application Data

(63) Continuation of application No. 15/853,118, filed on Dec. 22, 2017, now Pat. No. 10,233,493, which is a continuation of application No. 15/132,662, filed on Apr. 19, 2016, now Pat. No. 9,862,998, which is a continuation of application No. 13/162,325, filed on Jun. 16, 2011, now Pat. No. 9,353,412.

(60) Provisional application No. 61/437,441, filed on Jan. 28, 2011, provisional application No. 61/433,025, filed on Jan. 14, 2011, provisional application No. 61/356,178, filed on Jun. 18, 2010.

(51) Int. Cl.
*C12P 19/34* (2006.01)
*C12Q 1/6874* (2018.01)
*C12Q 1/6806* (2018.01)
*C12Q 1/6818* (2018.01)

(52) U.S. Cl.
CPC ......... *C12Q 1/6874* (2013.01); *C12Q 1/6806* (2013.01); *C12Q 1/6818* (2013.01)

(58) Field of Classification Search
None
See application file for complete search history.

(56) References Cited

U.S. PATENT DOCUMENTS

| | | | |
|---|---|---|---|
| 5,641,658 A | 6/1997 | Adam et al. | |
| 6,210,891 B1 | 4/2001 | Nyren et al. | |
| 6,908,736 B1 | 6/2005 | Densham | |
| 7,057,026 B2 | 6/2006 | Barnes et al. | |
| 7,115,400 B1 | 10/2006 | Adessi et al. | |
| 7,329,492 B2 | 2/2008 | Hardin et al. | |
| 7,414,116 B2 | 8/2008 | Milton et al. | |
| 7,427,673 B2 | 9/2008 | Balasubramanian et al. | |
| 7,604,963 B2 | 10/2009 | Densham | |
| 2002/0055100 A1 | 5/2002 | Kawashima et al. | |
| 2004/0002090 A1 | 1/2004 | Mayer et al. | |
| 2004/0096853 A1 | 5/2004 | Mayer | |
| 2005/0130173 A1 | 6/2005 | Leamon et al. | |
| 2007/0128624 A1 | 6/2007 | Gormley et al. | |
| 2008/0009420 A1 | 1/2008 | Schroth et al. | |
| 2009/0087850 A1 | 4/2009 | Eid et al. | |
| 2009/0286245 A1 | 11/2009 | Bjorson et al. | |
| 2010/0173303 A1 | 7/2010 | Ronachi et al. | |
| 2010/0279882 A1 | 11/2010 | Ronaghi et al. | |
| 2010/0330570 A1 | 12/2010 | Vander Horn et al. | |
| 2011/0160077 A1 | 6/2011 | Chaisson et al. | |
| 2011/0294116 A1 | 12/2011 | Huang et al. | |

FOREIGN PATENT DOCUMENTS

| | | |
|---|---|---|
| EP | 1681356 | 7/2006 |
| WO | 1991006678 | 5/1991 |
| WO | 0125480 | 4/2001 |
| WO | 2005010145 | 2/2005 |
| WO | 20009056831 | 5/2009 |
| WO | 2009111440 | 9/2009 |

(Continued)

OTHER PUBLICATIONS

"International Search Report and Written Opinion for PCT/US2011/0404765", International Searching Authority, dated Sep. 1, 2011.
Agah, et al., "A multi-enzyme model for pyrosequencing", Nucl. Acids Res. vol. 32 No. 21 e166, 2004.
Berde, et al., "Human alpha-Fetoprotein", J. Biol. Chem. 254 (24), 1979, 12609-12613.
Eid, J. et al., "Real-Time DNA Sequencing from Single Polymerase Molecules", Science 323,, 2009, 133-138.

(Continued)

*Primary Examiner* — Kenneth R Horlick
(74) *Attorney, Agent, or Firm* — Gavrilovich, Dodd & Lindsey LLP

(57) ABSTRACT

This disclosure provides a method of determining a sequence of nucleotides for a nucleic acid template. The method can include the steps of contacting the nucleic acid template with a conformationally labeled polymerase and at least four different nucleotide species under conditions wherein the conformationally labeled polymerase catalyzes sequential addition of the nucleotide species to form a nucleic acid complement of the nucleic acid template, wherein the sequential addition of each different nucleotide species produces a conformational signal change from the conformationally labeled polymerase and wherein the rate or time duration for the conformational signal change is distinguishable for each different nucleotide species; detecting a series of changes in the signal from the conformationally labeled polymerase under the conditions; and determining the rates or time durations for the changes in the signal, thereby determining the sequence of nucleotides for the nucleic acid template.

18 Claims, 15 Drawing Sheets

(56) References Cited

FOREIGN PATENT DOCUMENTS

| WO | 2009145820 | 12/2009 |
|---|---|---|
| WO | 2010068884 | 6/2010 |

OTHER PUBLICATIONS

Flusberg, et al., "Direct detection of DNA methylation during single-molecule, real-time sequencing", Nat. Meth. DOI10.1038/NMETH.1459, 2010.

Flusberg, et al., "Direct detection of DNA methylation during single-molecule, real-time sequencing", Nature Methods: doi:10.1038/nmeth.1459, Supplementary figures and text:, 12, 2010.

Gardner, et al., "Comparative Kinetics of Nucleotide Analog Incorporation by Vent DNA Polymerase", The Journal of Biological Chemistry, vol. 279, No. 12, Mar. 19, 2004, 11834-11842.

Ha, et al., "Temporal Fluctuations of Fluorescence Resonance Energy Transfer Between Two Dyes Conjugated to a Single Protein", Chem. Phys. 247, 1999, 107-118.

Hohlbein, "Single molecule FRET reveals conformational transitions in DNA polymerase I", Kapanidis lab, Department of Physics, University of Oxford, May 2010.

Hohlbein, "Towards dark-quencher based real-time DNA sequencing", University of Oxford, Feb. 2010.

Hwang, et al., "Substituent effects on the pairing and polymerase recognition of simple unnatural base pairs", Nucleic Acids Research, vol. 34, No. 7, 2006, 2037-2045.

Joyce, et al., "Fingers-Closing and Other Rapid Conformational Changes in DNA Polymerase I (Klenow Fragment) and Their Role in Nucleotide Selectivity", Biochemistry, 47, 2008, 6103-6116.

Krueger, et al., "Redesigning the architecture of the base pair: toward biochemical and biological function of new genetic sets", Chem Biol. 16, 2009, 242-8.

Lizardi, , "Mutation detection and single-molecule counting using isothermal rolling-circle amplification", Nature Genetics, vol. 19, 1998, 225-232.

Mulder, et al., "Nucleotide modification at the y-phosphate leads to the improved fidelity of HIV-1 reverse transcriptase", Nucleic Acids Res. 33, No. 15, 2005, 4865-4873.

Patro, et al., "Role of the 2-Amino Group of Purines during dNTP Polymerization by Human DNA Polymerase .alpha . . . dagger.", Biochemistry 48(1):180-189, Jan. 13, 2009.

Santoso, Yusdi , "Conformational Transitions in DNA Polymerase I Revealed by Single-Molecule FRET", Proceedings of the National Academy of Sciences; vol. 107, No. 2, Jan. 12, 2010, 715-720.

Wang, et al., "Crystal Structure of a Pol Family Replication DNA Polymerase from Bacteriophase RB69", Cell, 89(7), 1997, 1087-1099.

Wang, et al., "Pre-Steady-State Kinetics of RB69 DNA Polymerase and ITs Exo Domain Mutants: Effect of pH and Thiophosphoryl Linkages on 3'-5' Exonuclease Activity", Biochemistry 43, 2004, 3853-3861.

α-boranotriphosphate

α-phosphorothioate

β,γ-Halomethylene bridged triphosphate

γ-phosphate of the triphosphate

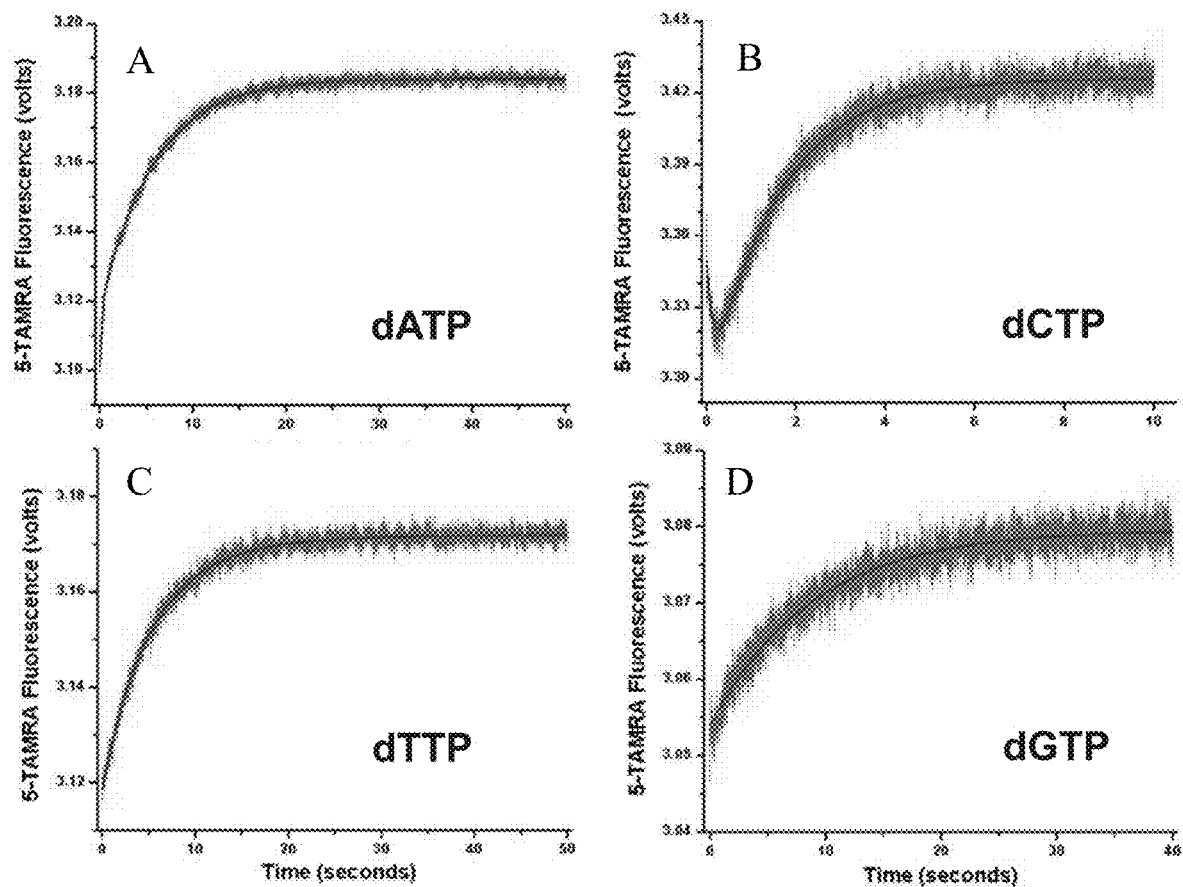
FIG. 10A-D

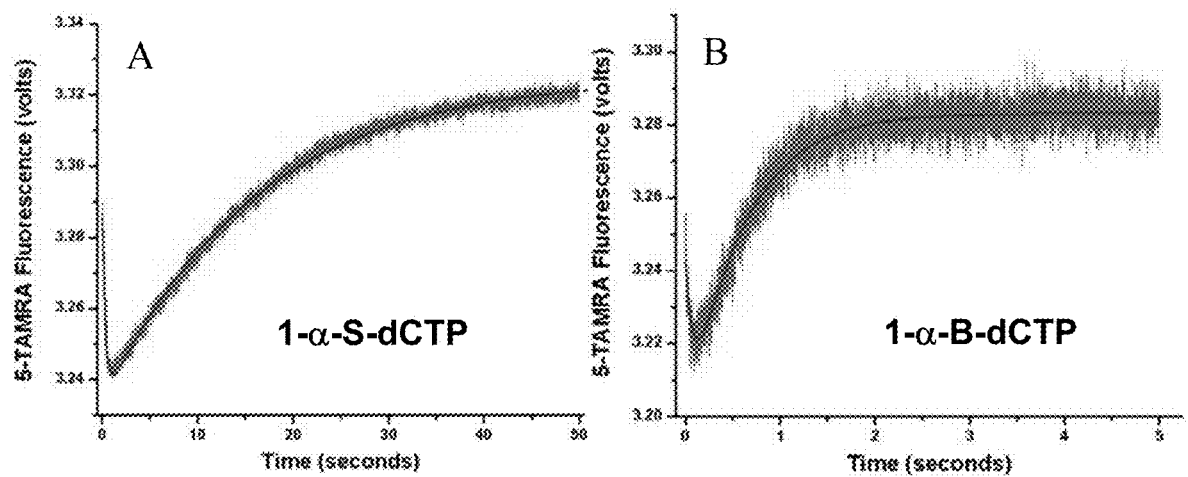
*FIG. 11A*  *FIG. 11B*
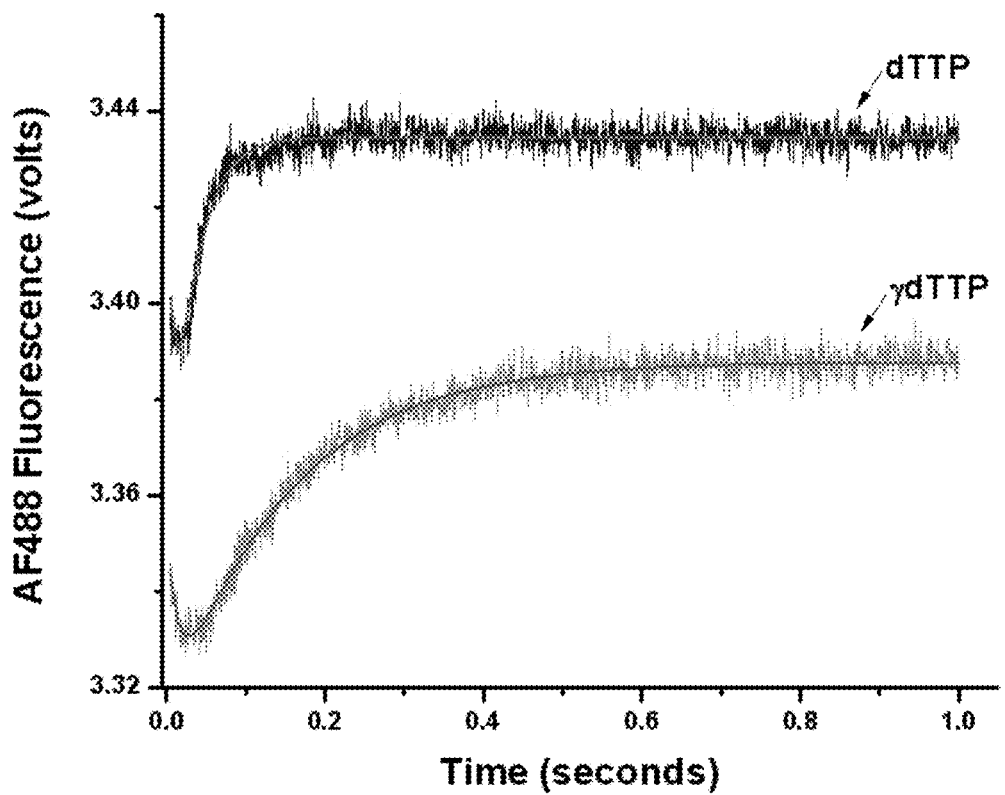
*FIG. 12*

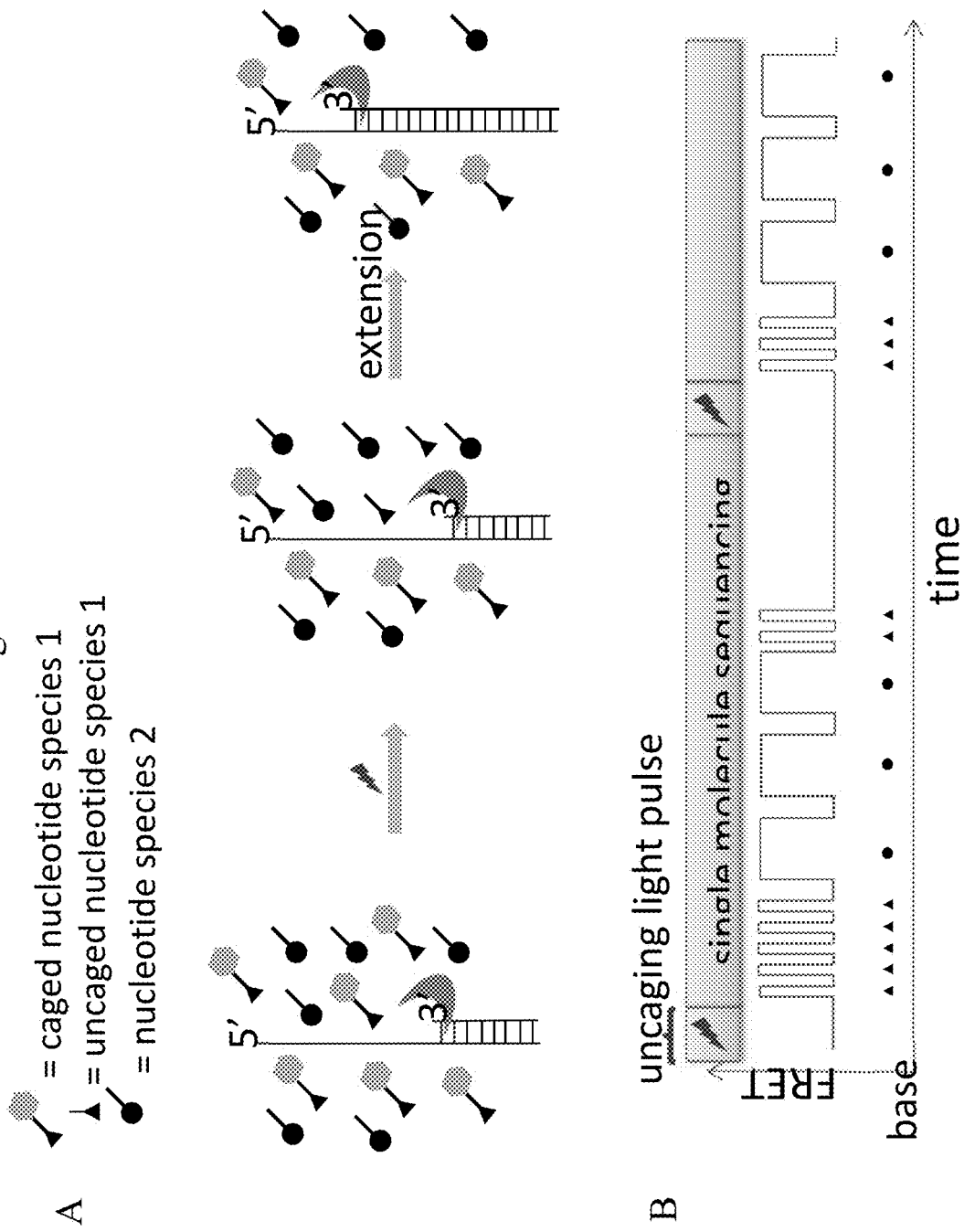
Figure 14A-B

CONFORMATIONAL PROBES AND METHODS FOR SEQUENCING NUCLEIC ACIDS

CROSS REFERENCE TO RELATED APPLICATIONS

This application is a continuation of, and claims the benefits and priority to, U.S. patent application Ser. No. 15/853,118, filed Dec. 22, 2017, which is a continuation of U.S. application Ser. No. 15/132,662, filed Apr. 19, 2016, which is a continuation of U.S. application Ser. No. 13/162,325, filed Jun. 16, 2011, which claims priority to U.S. Provisional Application Ser. No. 61/356,178, filed Jun. 18, 2010; 61/433,025 filed Jan. 14, 2011, and 61/437,441, filed Jan. 28, 2011, each of which is incorporated herein by reference in its entirety.

BACKGROUND

This disclosure relates generally to evaluation of nucleic acids and enzymes that catalyze reactions having nucleic acids as their reactants or products. More specifically this disclosure relates to sequencing nucleic acids, evaluating activity of polymerases or other enzymes, or combinations thereof.

Our genome provides a blue print with boundless potential for predicting many of our inherent predispositions such as our likes, dislikes, talents, emotional inclinations and susceptibility to disease. Our ability to decipher the blue print is slowly improving through improvements in nucleic acid sequencing technologies. However, to date only a handful of human genomes have been sequenced. Having one or even 100 genome sequences is scientifically interesting because it provides clues to unraveling the symbols and features that make up the blue print. However, a more complete understanding of how the information in each blue print relates to the living structures they encode, will require that tens-of-thousands or millions of genomes be sequenced. Only then will scientists be able to correlate the complexities of the genetic code with the variety of human characteristics.

With sufficient numbers of genomic sequences of many different people, researchers will be able to identify the appropriate correlations to (a) guide individuals in making proper choices for preventive medicine, (b) develop targeted drugs and other treatments that are specific and effective, and avoid side effects and drug resistance, and (c) reduce the costs to society and the individual in implementing effective therapies based on an individual's genomic predispositions.

The day when each person can sit down with a doctor to review a copy of their own personal genome and determine appropriate choices for a healthy lifestyle or a proper course of treatment for a presenting disease is not here yet. First the time and cost for determining genomic sequences must come down to a level that large genetic correlation studies can be carried out by scientists. Furthermore, the technology must reach the point that it is accessible to virtually anyone in a clinical environment regardless of economic means and personal situation.

Thus, there exists a need for improved nucleic acid sequencing techniques. The present invention satisfies this need and provides other advantages as well.

BRIEF SUMMARY

This disclosure provides a method of determining a sequence of nucleotides for a nucleic acid template. The method can include the steps of contacting the nucleic acid template with a conformationally labeled polymerase and at least four different nucleotide species under conditions wherein the conformationally labeled polymerase catalyzes sequential addition of the nucleotide species to form a nucleic acid complement of the nucleic acid template, wherein the sequential addition of each different nucleotide species produces a conformational signal change from the conformationally labeled polymerase and wherein the rate or time duration for the conformational signal change is distinguishable for each different nucleotide species; detecting a series of changes in the signal from the conformationally labeled polymerase under the conditions; and determining the rates or time durations for the changes in the signal, thereby determining the sequence of nucleotides for the nucleic acid template. The method can also be used to identify modified bases within a sequence such as methylated bases.

Also provided herein is a method of determining a sequence of nucleotides for a nucleic acid template. The method can include the steps of contacting the nucleic acid template with a conformationally labeled exonuclease under conditions wherein the conformationally labeled exonuclease catalyzes sequential removal of nucleotide species from the nucleic acid template, wherein the sequential removal of each different nucleotide species produces a conformational signal change from the conformationally labeled exonuclease and wherein the rate or time duration for the conformational signal change is distinguishable for each different nucleotide species that is removed; detecting a series of changes in the signal from the conformationally labeled exonuclease under the conditions; and determining the rates or time durations for the changes in the signal for the series of changes in the signal from the conformationally labeled exonuclease, thereby determining the sequence of nucleotides for the nucleic acid template. The method can also be used to identify modified bases within a sequence such as methylated bases.

This disclosure further provides a method of determining a sequence of nucleotides for a nucleic acid template. The method can include the steps of contacting the nucleic acid template with a conformationally labeled polymerase and at least four different nucleotide species under conditions wherein the conformationally labeled polymerase catalyzes sequential addition of the nucleotide species to form a nucleic acid complement of the nucleic acid template, wherein the sequential addition of each different nucleotide species produces a conformational signal change from the conformationally labeled polymerase and wherein the rate or time duration for the conformational signal change is distinguishable for each different nucleotide species; detecting a series of changes in the signal from the conformationally labeled polymerase under the conditions; determining the rates or time durations for the changes in the signal, thereby determining the sequence of nucleotides for the nucleic acid template; contacting the nucleic acid template with a conformationally labeled exonuclease under conditions wherein the conformationally labeled exonuclease catalyzes sequential removal of nucleotide species from the nucleic acid template, wherein the sequential removal of each different nucleotide species produces a conformational signal change from the conformationally labeled exonuclease and wherein the rate or time duration for the conformational signal change is distinguishable for each different nucleotide species that is removed; detecting a series of changes in the signal from the conformationally labeled exonuclease under the conditions; and determining the rate or time durations for the changes in the signal for the series of changes in the signal from the conformationally labeled exonuclease. The method can also be used to identify modified bases within a sequence such as methylated bases.

In a further embodiment a method of determining a sequence of nucleotides for a nucleic acid sample is provided. The method can include the steps of providing an array of nucleic acid templates, wherein the nucleic acid templates include nucleotide sequence fragments of the nucleic acid sample; contacting the array of nucleic acid templates with conformationally labeled polymerases and at least four different nucleotide species under conditions wherein the conformationally labeled polymerases catalyze sequential addition of the nucleotide species to form nucleic acid complements of the nucleic acid templates, wherein the sequential addition of each different nucleotide species produces a conformational signal change from the conformationally labeled polymerase and wherein the rate or time duration for the conformational signal change is distinguishable for each different nucleotide species; detecting a series of changes in the signal from the conformationally labeled polymerase under the conditions and at individual locations of the array; and determining the rates or time durations for the changes in the signal at the individual locations of the array, thereby determining the sequence of nucleotides for the nucleic acid sample. The method can also be used to identify modified bases within a sequence such as methylated bases.

Also provided is a method of determining nucleotide sequences which can optionally include the steps of (a) providing an array of nucleic acid templates; (b) providing a mixture of nucleotide species, the mixture including (i) at least four different nucleotide species, (ii) at least one of the four different nucleotide species having a reversible terminator moiety, and (iii) at least two of the four different nucleotide species having an extendible 3' hydroxyl moiety; (c) contacting the array of nucleic acid templates with conformationally labeled polymerases and the mixture of nucleotide species under conditions wherein the conformationally labeled polymerases catalyze sequential addition of the nucleotide species to form nucleic acid complements of the nucleic acid templates, wherein the sequential addition of each different nucleotide species produces a conformational signal change from the conformationally labeled polymerase, wherein the rate or time duration for the conformational signal change is distinguishable for the at least two nucleotide species having the extendible 3' hydroxyl moiety, and wherein a plurality of the nucleic acid complements incorporate the at least one nucleotide species that has the reversible terminator moiety; (d) removing the reversible terminator moiety; (e) detecting a series of changes in the signal from the conformationally labeled polymerase at individual locations of the array; and (f) determining the sequence of nucleotides for the nucleic acid sample from the series of changes in the signal from the conformationally labeled polymerase.

BRIEF DESCRIPTION OF THE DRAWINGS

FIG. 10A-D shows a plot of 5-TAMRA fluorescence vs. time for incorporation of natural nucleotides into a template bound primer by a conformationally labeled polymerase.
FIG. 11A-B shows a plot of 5-TAMRA fluorescence vs. time for incorporation of non-natural nucleotides into a template bound primer by a conformationally labeled polymerase.
FIG. 12 shows a plot of donor fluorescence vs. time for incorporation of dTTP and γ-dTTP into a template bound primer by a conformationally labeled polymerase.
FIG. 14A-B shows a method for light-gated sequencing.

DETAILED DESCRIPTION OF EMBODIMENTS

Figure 1:
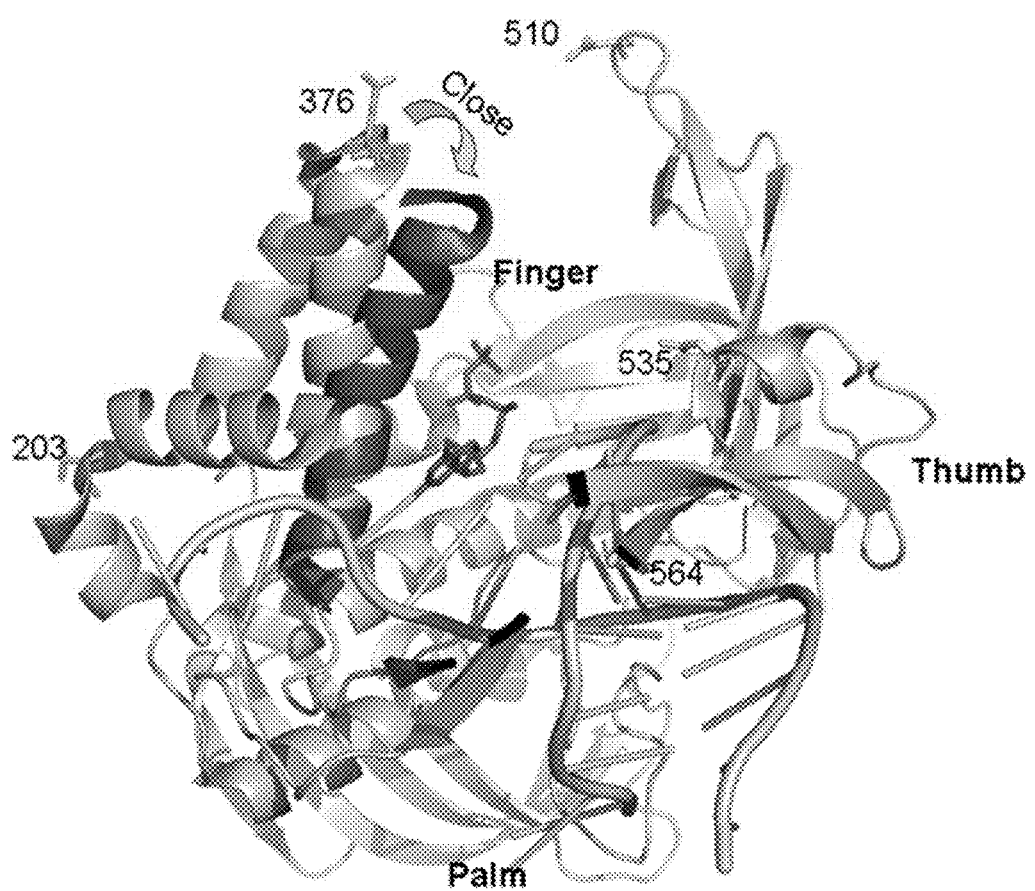
FIG. 1 shows a molecular model of Phi29 polymerase.

This disclosure provides methods useful for determining the nucleotide sequences of nucleic acid molecules. The methods can be used to identify the nucleotide sequence for a single species of nucleic acid, for example, present in a reaction vessel or attached to a solid support. For purposes of illustration, the methods will often be exemplified in the context of steps carried out for a single nucleic acid molecule or single species of nucleic acid molecule. However, the methods set forth herein are useful for multiplex detection whereby the steps are carried out simultaneously for several different nucleic acids. The methods can be carried out at a multiplex level that allows a substantial portion, or in some cases an entire genome, to be sequenced simultaneously. Furthermore, whether or not multiplex detection is carried out, detection can occur at a single molecule detection level or at a level whereby several species of a particular molecule are detected as an ensemble.

In particular embodiments, a sequence of nucleotides for a nucleic acid template can be determined based on conformational changes occurring in an enzyme that interacts with the nucleic acid. Such enzymes, often referred to as nucleic acid enzymes, can interact sequentially with the nucleotide subunits of a nucleic acid in order to carry out a series of reactions on the nucleic acid. Distinguishing the conformational changes that occur for each type of nucleotide that the enzyme interacts with and determining the sequence of those changes can be used to determine the sequence of the nucleic acid. For example, a polymerase can use a first nucleic acid strand as a template to sequentially build a second, complementary nucleic acid strand by sequential addition of nucleotides to the second strand. The polymerase undergoes conformational changes with each nucleotide addition. As set forth in further detail herein, the conformational changes that occur for each type of nucleotide that is added can be distinguished and the sequence of those changes can be detected to determine the sequence of either or both of the nucleic acid strands. In another example, an exonuclease can sequentially remove nucleotides from a nucleic acid. Conformational changes that occur for each type of nucleotide that is removed can be distinguished and the sequence of those changes can be detected to determine the sequence of the nucleic acid.

Also provided herein are compositions useful for determining the nucleotide sequences of nucleic acid molecules. An example is a nucleic acid enzyme that is labeled to produce one or more signals indicative of a conformational change in the enzyme as it interacts with one or more reactants such as a nucleic acid or nucleotide. For example, a polymerase can be conformationally labeled to allow detection of a signal indicative of nucleotide binding, a signal indicative of addition of a nucleotide to a growing nucleic acid molecule, or a signal indicative of an intermediate change in the conformation of the polymerase between binding and catalysis. In particular embodiments, the signal can distinguish a binding event from a catalytic event. However, such a distinction may not be necessary for some embodiments and the signal can be merely indicative of the overall addition of a nucleotide. Alternatively or additionally, the signal can distinguish binding of a correctly base-paired nucleotide from binding of an incorrectly base-paired nucleotide. Another example is an exonuclease that is conformationally labeled to allow detection of a signal indicative of catalytic breakage of a bond between a nucleotide and nucleic acid, a signal indicative of dissociation of the nucleotide from the exonuclease, or a signal indicative of an intermediate change in the conformation of the exonuclease between catalysis and dissociation. The exonuclease can be a polymerase acting under conditions to remove nucleotides from a nucleic acid, for example, via 3'→5' exonucleolytic cleavage activity. Again, in particular embodiments the catalytic event can be distinguished from the dissociation event, or the signal can be indicative of the overall removal of a nucleotide.

Another example of a useful type of composition is a nucleotide analog that is incorporated into a polynucleotide strand by a polymerase at a rate that is measurably different than the rate at which another nucleotide is incorporated into the strand by the polymerase. Another useful nucleotide analog is one that is bound to a polymerase at a rate that is measurably different than the rate at which another nucleotide is bound to the polymerase. A nucleotide analog that causes a conformational change of a polymerase at a rate that is measurably different than for another nucleotide is also useful. The relative rate of binding, incorporation or polymerase conformational change for a nucleotide analog can be measured relative to a natural nucleotide having the same Watson-Crick base pairing partner or relative to other nucleotides that are used in a nucleic acid synthesis reaction. The relative rate can be faster or slower for the nucleotide analog. A nucleotide analog that is removed from a nucleic acid by an exonuclease at a rate that is measurably faster or slower than the rate at which a natural nucleotide is removed from the nucleic acid is also useful. Another useful nucleotide analog is one that causes conformational change of an exonuclease at a rate that is measurably different than the rate for another nucleotide.

For purposes of demonstration several compositions, such as conformationally labeled molecules and nucleotide analogs, are described in the context of particular nucleic acid sequencing methods. It will be understood that the compositions set forth herein can be used in a variety of other sequencing methods. Moreover, the compositions can be used for any of a variety of applications such as those that will be apparent to those skilled in the art in view of the known or determinable properties of the compositions and the guidance set forth herein.

Terms used herein will be understood to take on their ordinary meaning unless specified otherwise. Examples of several terms used herein and their definitions are set forth below.

As used herein, the term "conformationally labeled," when used in reference to a molecule, means having at least one probe that is responsive to a change in the structure of the molecule, a change in the shape of the molecule or a change in the arrangement of parts of the molecule. The molecule can be, for example, a polymerase, reverse transcriptase, exonuclease or other nucleic acid enzyme such as those set forth herein below. The parts of the molecule can be, for example, atoms that change relative location due to rotation about one or more chemical bonds occurring in the molecular structure between the atoms. The parts of the molecule can be domains of a macromolecule such as those commonly known in the relevant art. For example, polymerases include domains referred to as the finger, palm and thumb domains. In the case of proteins the parts can be regions of secondary, tertiary or quaternary structure. The probe(s) can be attached to the molecule, for example, via a covalent linkage. However, the probe(s) need not be attached to the molecule, being, for example, located in proximity to the molecule. In particular embodiments the probe is not attached to a reactant or product of the molecule such as a nucleotide or nucleic acid.

As used herein, the term "conformational signal change," when used in reference to a conformationally labeled molecule, means the appearance, disappearance, or alteration of a detectable signal from a probe of the molecule in response to a change in the structure, shape or arrangement of parts of the molecule. For example, the signal change can be due to a change in the interaction of the probe with a first portion of the molecule to interact with a second portion of the molecule. The term, when specifically recited, is intended to distinguish from changes in signal that arise from a probe of a molecule due to a change in the interaction of the probe with a reactant that binds specifically to the molecule or a change in the interaction of the probe with a product that results from catalytic activity of the molecule. For example, the term, when specifically recited, can be used to exclude a change in a fluorescence resonance energy transfer signal that arises from a donor or acceptor probe of a polymerase changing its interaction with an acceptor or donor probe, respectively, on a nucleic acid or nucleotide. Also by way of example, the term, when specifically recited, can be used to exclude a change in a fluorescence signal that arises from a probe on a polymerase or quencher on a polymerase that changes its interaction with a quencher or probe, respectively, on a nucleic acid or nucleotide.

As used herein, the term "position," when used in reference to a protein, means a location for a particular amino acid residue in the structure of the protein. The term can be used to describe the location independent of the type of amino acid residue that is present at the position. Thus, the position can be occupied by an amino acid residue that is found in a wild-type protein or the position can be occupied by another amino acid residue due to a mutation at the position. Furthermore, the term can be used to describe a location that is homologous across two or more proteins of the same type. Homologous locations are known or identifiable to those in the art based on structural comparison between proteins of the same type. For example, position 486 in Pfu DNA polymerase is homologous to 485 in 9° N DNA polymerase, position 488 in Vent DNA polymerase, and position 485 in JDF-3 DNA polymerase. The term "position" can also be used in reference to a nucleic acid in order to identify the location for a particular nucleotide in the sequence of the nucleic acid. The location can be identified independent of the type of nucleotide that is present at the position.

As used herein, the term "species" is used to identify molecules that share the same chemical structure. For example, a mixture of nucleotides can include several dCTP molecules. The dCTP molecules will be understood to be the same species as each other. Similarly, individual DNA molecules that have the same sequence of nucleotides are the same species.

As used herein, the term "complement" or grammatical variations thereof can be used to describe the characteristic of a nucleic acid whereby its bases precisely pair with those of a second nucleic acid. For two nucleic acid strands that are complementary the sequence of bases for one strand can be used to determine the sequence of bases for the other. Complementarity includes for example base pairing between naturally occurring bases such as the pairing of cytosine with guanine and the pairing of adenine with thymine. However, complementarity can also occur between nucleotide analogs having non-natural bases. For example, a nucleic acid strand having non-natural bases can form a complement to a second strand having natural bases such that the sequence of bases for the former can be used to determine the nucleotide sequence for the latter and vice versa. Complementarity can be, but need not necessarily be, perfect for particular embodiments set forth herein. For example, two nucleic acids can have at least about 75% complementarity, at least about 80% complementarity, at least about 85% complementarity, at least about 90% complementarity, at least about 95% complementarity, at least about 98% complementarity, or 100% complementarity.

As used herein, the term "array" refers to a population of different molecules that are attached to one or more solid-phase substrates such that the different molecules can be differentiated from each other according to their relative location. An array can include different molecules that are each located at a different addressable location on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be nucleic acid primers, nucleic acid probes, nucleic acid templates or nucleic acid enzymes such as polymerases and exonucleases.

As used herein, the term "nucleic acid fragment" includes a nucleic acid that has a portion of contiguous sequence from a larger nucleic acid. The fragment can be a piece that is removed from a larger molecule, for example, by physical shearing, chemical cleavage or enzymatic (nuclease) cleavage. A fragment can also be a product of amplifying a region or portion of a larger sequence, for example, using PCR primers that hybridize to sites within a chromosome such that a region internal to the chromosome is amplified and flanking regions are not. A fragment can also be a product of a transposase reaction such as a reaction described in Adey et al. *Genome Biology* 11:R119 (2010) and U.S. Pat. No. 5,965,443 or 6,437,109, each of which is incorporated herein by reference.

As used herein, the term "nucleotide" is intended to include natural nucleotides, analogs thereof, ribonucleotides, deoxyribonucleotides, dideoxyribonucleotides and other molecules known as nucleotides. The term can be used to refer to a monomeric unit that is present in a polymer, for example to identify a subunit present in a DNA or RNA strand. The term can also be used to refer to a molecule that is not necessarily present in a polymer, for example, a molecule that is capable of being incorporated into a polynucleotide in a template dependent manner by a polymerase. The term can refer to a nucleoside unit having, for example, 0, 1, 2, 3 or more phosphates on the 5' carbon. For example, tetraphosphate nucleotides and pentaphosphate nucleotides can be particularly useful. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides also referred to herein as nucleotide analogs, include those that are not present in a natural biological system or not substantially incorporated into polynucleotides by a polymerase in its natural milieu, for example, in a non-recombinant cell that expresses the polymerase. Particularly useful non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different or more when compared to the incorporation rate of a natural nucleotide, such as one or more of those exemplified above. A non-natural nucleotide can be capable of being further extended after being incorporated into a polynucleotide. Examples include, nucleotide analogs having a 3' hydroxyl or nucleotide analogs having a reversible blocking group at the 3' position that can be removed to allow further extension of a polynucleotide that has incorporated the nucleotide analog. Examples of reversible blocking groups that can be used are described, for example, in U.S. Pat. Nos. 7,427,673; 7,414,116; and 7,057,026 and PCT publications WO 91/06678 and WO 07/123744, each of which is incorporated herein by reference. It will be understood that in some embodiments a nucleotide analog having a 3' blocking group or lacking a 3' hydroxyl (such as a dideoxynucleotide analog) can be used under conditions where the polynucleotide that has incorporated the nucleotide analog is not further extended. In some embodiments, the nucleotide(s) will not include a reversible blocking group, or the nucleotides(s) will not include a non-reversible blocking group or the nucleotide(s) will not include any blocking group at all.

Provided herein is a method of determining a sequence of nucleotides for a nucleic acid template. The method can include the steps of contacting the nucleic acid template with a conformationally labeled polymerase and at least four different nucleotide species under conditions wherein the conformationally labeled polymerase catalyzes sequential addition of the nucleotide species to form a nucleic acid complement of the nucleic acid template, wherein the sequential addition of each different nucleotide species produces a conformational signal change from the conformationally labeled polymerase and wherein the rate or time duration for the conformational signal change is distinguishable for each different nucleotide species; detecting a series of changes in the signal from the conformationally labeled polymerase under the conditions; and determining the rates or time durations for the changes in the signal, thereby determining the sequence of nucleotides for the nucleic acid template.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases. Exemplary DNA polymerases include those that have been classified by structural homology into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase. Family C includes, for example, the *E. coli* DNA Polymerase III alpha subunit. Family D includes, for example, polymerases derived from the Euryarchaeota subdomain of Archaea. DNA Polymerases in Family X include, for example, eukaryotic polymerases Pol β, pol σ, Pol λ, and Pol μ, and *S. cerevisiae* Pol4. DNA Polymerases in Family Y include, for example, Pol η, Pol iota, Pol kappa, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

The above classifications are provided for illustrative purposes. It will be understood that variations in the classification system are possible. For example, in at least one classification system Family C polymerases have been categorized as a subcategory of Family X. Furthermore, polymerases can be classified according to other characteristics, whether functional or structural, that may or may not overlap with the structural characteristics exemplified above. Some exemplary characteristics are set forth in further detail below.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein. Polymerases can also catalyze pyrophosphorolysis, the direct reversal of polymerization in the same active site. This activity can be useful for various embodiments that are set forth herein.

Polymerases can be characterized according to their processivity. A polymerase can have an average processivity that is at least about 50 nucleotides, 100 nucleotides, 1,000 nucleotides, 10,000 nucleotides, 100,000 nucleotides or more. Alternatively or additionally, the average processivity for a polymerase used as set forth herein can be, for example, at most 1 million nucleotides, 100,000 nucleotides, 10,000 nucleotides, 1,000 nucleotides, 100 nucleotides or 50 nucleotides. Polymerases can also be characterized according to their rate of processivity or nucleotide incorporation. For example, many native polymerases can incorporate nucleotides at a rate of at least 1,000 nucleotides per second. In some embodiments a slower rate may be desired. For example, an appropriate polymerase and reaction conditions can be used to achieve an average rate of at most 500 nucleotides per second, 100 nucleotides per second, 10 nucleotides per second, 1 nucleotide per second, 1 nucleotide per 10 seconds, 1 nucleotide per minute or slower. As set forth in further detail elsewhere herein, nucleotide analogs can be used that have slower or faster rates of incorporation than naturally occurring nucleotides. It will be understood that polymerases from any of a variety of sources can be modified to increase or decrease their average processivity or their average rate of processivity (e.g. average rate of nucleotide incorporation) or both. Accordingly, a desired reaction rate can be achieved using appropriate polymerase(s), nucleotide analog(s), nucleic acid template(s) and other reaction conditions.

Depending on the embodiment that is to be used, a polymerase can be either thermophilic or heat inactivatable. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. It will be understood that polymerases from any of a variety of sources can be modified to increase or decrease their tolerance to high temperature conditions.

Polymerases can be characterized according to their fidelity. Fidelity generally refers to the accuracy with which a polymerase incorporates correct nucleotides into a copy of a nucleic acid template. DNA polymerase fidelity can be measured as the ratio of correct to incorrect nucleotide incorporations when the nucleotides are present at equal concentrations to compete for primer extension at the same site in the polymerase-primer-template DNA binary complex. As proposed by Fersht, DNA polymerase fidelity can be calculated as the ratio of $(k_{cat}/K_m)$ for the correct nucleotide and $(k_{cat}/K_m)$ for the incorrect nucleotide; where $k_{cat}$ and $K_m$ are the familiar Michaelis-Menten parameters in steady state enzyme kinetics (Fersht, A. R. (1985) *Enzyme Structure and Mechanism,* 2nd ed., p 350, W. H. Freeman & Co., New York, incorporated herein by reference). Alternatively, in pre-steady state measurements, the ratio of $(k_{pol}/K_d)$ for the correct and incorrect nucleotides can be used. In particular embodiments, a polymerase can have a fidelity value at least 100, 1000, 10,000, 100,000, or 1 million, with or without a proofreading activity.

According to particular embodiments, a polymerase or other molecule can be conformationally labeled. Conformational labeling of nucleic acid enzymes provides advantages for nucleic acid sequence analysis. Conformationally labeled molecules, and methods for making and using them, will be exemplified below with regard to labeled polymerases. It will be understood that other nucleic acid enzymes such as exonucleases and reverse transcriptases can be made and used similarly.

Polymerases undergo conformational changes in the course of synthesizing a nucleic acid polymer. For example, polymerases undergo a conformational change from an open conformation to a closed conformation upon binding of a nucleotide. Thus, a polymerase that is bound to a nucleic acid template and growing primer is in what is referred to in the art as an "open" conformation. A polymerase that is bound to a nucleic acid template, primer and a correctly base paired nucleotide is in what is referred to in the art as a "closed" conformation. At a more detailed structural level, the transition from the open to closed conformation is characterized by relative movement within the polymerase resulting in the "thumb" domain and "fingers" domain being closer to each other. In the open conformation the thumb domain is further from the fingers domain, akin to the opening and closing of the palm of a hand. In various polymerases, the distance between the tip of the finger and the thumb can change up to 10 angstroms between the "open" and "closed" conformations. The distance between the tip of the finger and the rest of the protein domains can also change up to 10 angstroms. It will be understood that larger changes may also occur and can be exploited in a method set forth herein such that a change that is greater than 10 angstroms can be detected. Furthermore, smaller changes can be detected including those that are less than about 10, 8, 6, 4, or 2 angstroms so long as the change in distance is sufficient to be detectable using the techniques employed.

In particular embodiments, a probe that is attached to a finger domain can be attached to a residue at position 376 or residues within 5 angstroms radius from position 376 of the Phi29 DNA polymerase and a probe that is attached to the thumb or other domain can be attached to a residue at position 535, 203, 510, 564, or residues within 5 angstroms radius from these positions of the Phi29 DNA polymerase. A molecular model showing some structural elements of Phi29 DNA polymerase and their relative locations is provided in FIG. 1. For clarity, the polymerase structure in the figure is reduced to elements that illustrate some relevant features of finger domain movements. The conformation of the polymerase in the open structure is shown in light grey. Upon the incoming nucleotide binding, the finger domain in the binary complex of polymerase and DNA moves closer to the thumb domain as indicated by the arrow labeled "close." The resulting conformation for the finger domain is indicated by the dark grey helical structure. Some candidate positions for attachment of probes are also labeled. It will be understood that homologous positions of these residues exemplified above can be used for other polymerases such as positions 550 and 744 in the Klenow Fragment.

In particular embodiments, a probe that is attached to a finger domain can be attached to a residue at position 325 of Pol beta DNA polymerase. This position has been shown to be sensitive to the environmental changes caused by polymerase reactions. It will be understood that homologous positions of the environmental sensitive residues exemplified above can be used for other polymerases such as the position 514 of the T7 DNA polymerase and 845 of the *Bacillus stearothermophilus* DNA polymerase. Other useful polymerases and locations on polymerases for conformational labels are described in U.S. Pat. No. 6,908,763 and WO 2010/068884 A2, each of which is incorporated herein by reference.

A change in conformation of a polymerase, for example, from an open conformation to a closed conformation, can be detected using a conformational probe. Any label or probe can be used that is responsive to a change in the structure, shape or arrangement of amino acid residues such as the changes that occur between the open and closed conformations of a polymerase. For example, an optical probe such as a fluorescent probe can be used. The emission properties of a fluorescent probe can change in response to changes in the local environment of the fluorophore.

A conformationally labeled enzyme, such as a polymerase or exonuclease, can include a pair of optical probes. For example, a fluorophore that normally has a detectable emission will be reduced or even prevented from emitting fluorescence when it comes into contact with a quencher. Accordingly, a conformationally labeled polymerase can have a fluorophore that emits signal in either the open or closed conformation and that is quenched in the closed or open conformation, respectively. Similarly, a conformationally labeled polymerase can include a donor or acceptor fluorophore that forms one in a pair of fluorescence (or Förster) resonance energy transfer (FRET) probes. One of the probes in the FRET pair can be placed at the fingers domain and the other can be placed at the thumb domain such that a change in conformation from the open to closed conformation (or vice versa) can be detected based on change in the amount of energy that is transferred to the acceptor and/or the amount of emission that is detected from the donor.

Exemplary fluorophores include, but are not limited to, fluorescent nanocrystals; quantum dots; d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Exemplary quenchers include, but are not limited to, DACYL(4-(4'-dimethylaminophenylazo)benzoic acid), Black Hole Quenchers (Biosearch Technologies, Novato, Calif.), Qxl quenchers (Anaspec, Freemont, Calif.), Iowa black quenchers, DABCYL, BHQ1, BHQ2, QSY7, QSY9, QSY21, QSY35, BHQO, BHQ1, BHQ2, QXL680, ATTO540Q, ATTO580Q, ATTO612Q, DYQ660, DYQ661 and IR Dye QC-1 quenchers. Fluorescent probes (including donors, acceptors, and quenchers) and methods for their use including attachment to protein enzymes are described in *Molecular Probes: The Handbook* (Invitrogen, Carlsbad Calif.), which is incorporated herein by reference. A fluorophore, quencher or other probe that is used in a method or composition set forth herein can be an intrinsic probe that is present in a naturally occurring molecule being detected, such as a tryptophan residue in a polymerase or exonuclease.

Alternatively or additionally, one can use a probe that is exogenous to a polymerase, exonuclease or other molecule being detected. Thus, in some embodiments solely exogenous probes are detected such that endogenous probes are not detected, in other embodiments solely endogenous probes are detected such that exogenous probes are not detected and in some embodiments a combination of exogenous and endogenous probes are detected.

In particular embodiments, a split green fluorescent (GFP) protein can be attached to a polymerase such that a portion of the GFP is fused to the finger domain of the polymerase while the complementary portion of the GFP is fused to the thumb or other domains of the polymerase. When the polymerase is in "open" conformation, the GFP fragments are far apart and fluorescence is inhibited or abolished. When the polymerase is in the "closed" conformation the GFP fragments are brought together and fluorescence appears or increases. The presence, absence, increase or decrease of fluorescence can be detected in a method set forth herein. Other variants of GFP such as wavelength shifted variants can be used similarly.

A probe can be attached to a polymerase, for example, via covalent linkage. Alternatively or additionally, a probe can be attached to another molecule that is in proximity to a polymerase, such that a conformational change in the polymerase causes a change in signal from the probe. For example, the polymerase can be attached to a solid support and the solid support can have a probe that is capable of interacting with the polymerase in a way that signals from the probe change in response to conformational changes of the polymerase. In a particular embodiment, a probe can be attached site specifically to a polymerase by introducing cysteine residue at a desired location in the polymerase and then modifying the polymerase with a probe having a moiety that reacts specifically with the sulfur group of cysteine, an exemplary reactive moiety being a reactive maleimide moiety. An exemplary method for introducing a FRET probe pair (Cy3B and atto 647N) into a polymerase using site specific cysteine mutagenesis followed by chemical modification with dyes having maleimide moieties is described in Santoso et al. *Proc. Nat'l. Acad. Sci. USA* 107:705-710 (2010), which is incorporated herein by reference. Probes can also be introduced to polymerase, exonuclease or other nucleic acid enzyme by split inteins as described in Yang et al. *J. Am. Chem. Soc.,* 131:11644-11645 (2009), which is incorporated herein by reference. Probes can also be introduced to nucleic acid enzymes by genetically encoded unnatural amino acids. One example is described in Fleissner et al. *Proc. Nat'l. Acad. Sci. USA* 106:21637-42 (2009), which is incorporated herein by reference.

Labels other than fluorescent labels can be used. For example, a polymerase or other nucleic acid enzyme can be labeled site specifically by paramagnetic spin labels such as nitroxide, and the conformational changes of the enzyme can be detected by observing changes in the relaxation time of the spin label using electron paramagnetic resonance and related techniques. Exemplary spin labels and techniques for their detection are described in Hubbell et al. *Trends Biochem Sci.* 27:288-95 (2002), which is incorporated herein by reference.

A change in signal that is detected from an optical probe due to a conformational change can be, for example, a change in wavelength or intensity. In particular embodiments, the change in wavelength can be a shift in excitation wavelength maximum, change in excitation spectrum, shift in emission wavelength maximum, or change in emission spectrum. The intensity change can be an increase in extinction coefficient, decrease in extinction coefficient, increase in quantum yield, or decrease in quantum yield. For example, a change in wavelength can be detected due to a change in proximity or orientation between a donor and acceptor of a FRET pair. A change in intensity of signal can be detected due to a change in proximity between a fluorophore and quencher or a change in orientation between a fluorophore and quencher. A change in wavelength or intensity can also be detected due to a change in structure, protonation state, or environment of a fluorophore. Exemplary changes in signal that can be detected in a method set forth herein include, without limitation, increased fluorescence resonance energy transfer (FRET, also referred to in the art as Förster resonance energy transfer), decreased FRET, increased fluorescence quenching or decreased fluorescence quenching. Detection of other forms of energy transfer can also be useful. Other changes in signal that can be detected from an optical probe due to a conformational change include a change in emission polarization, decrease in excited state lifetime, or increase in excited state lifetime.

Other labels and methods for detecting conformational changes in a polymerase are described in U.S. Pat. No. 6,908,763 and WO 2010/068884 A2, each of which is incorporated herein by reference. Although several embodiments of the methods set forth herein can utilize conformationally labeled polymerases, it will be understood that the label need not produce a conformational signal change. Accordingly, the labels and labeling techniques set forth herein can be used to label a polymerase or other nucleic acid enzyme in a method where conformational signal changes are not detected or distinguished.

Figure 2:
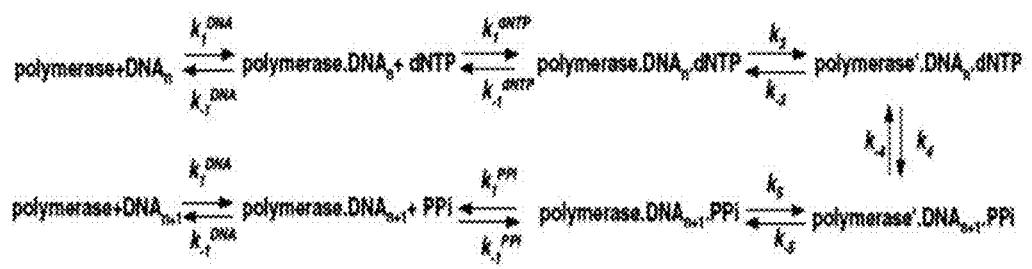
FIG. 2 shows a kinetic model of polymerase activity.
Figure 3A:
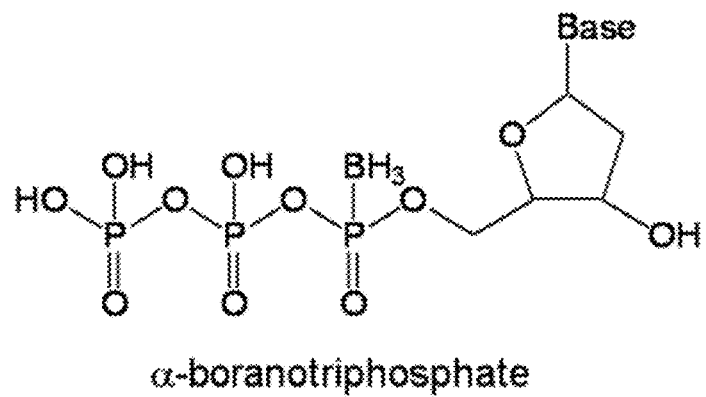
FIG. 3A-D shows triphosphates having chemical modifications at various positions.
Figure 3B:
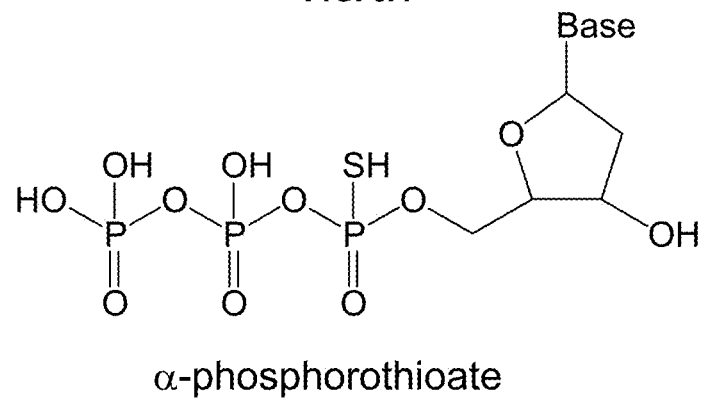
Figure 3C:
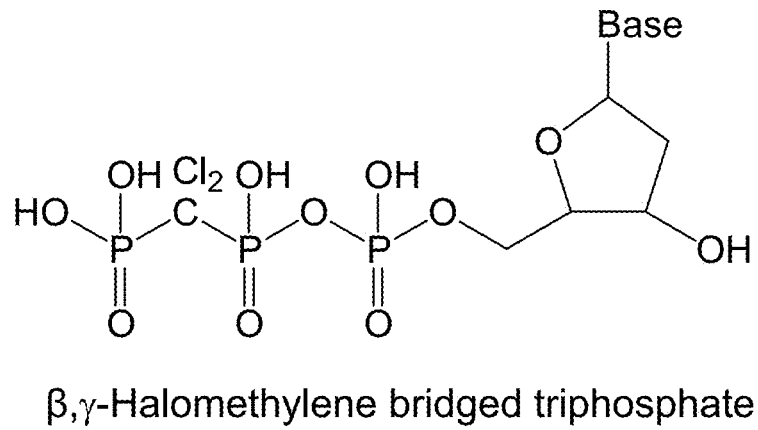
Figure 3D:
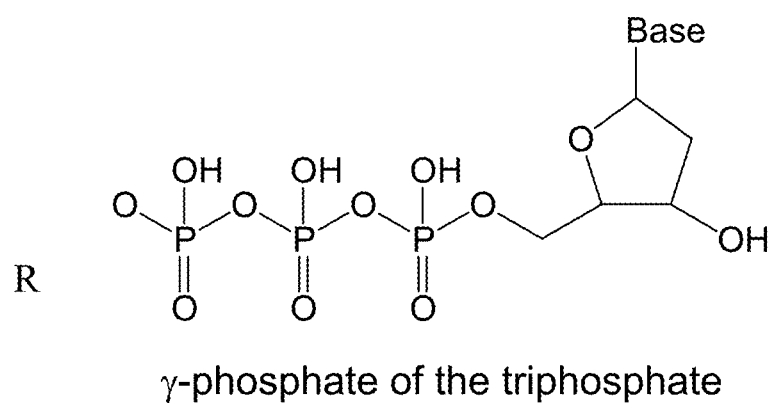

In addition to the conformational changes set forth herein and otherwise known in the art, polymerases undergo several transitions in the course of adding a nucleotide to a growing nucleic acid strand. The transitions can be distinguished from each other, for example, by kinetic characterization. As shown in FIG. 2, distinguishable transitions include, for example, the binding of primed nucleic acid to the polymerase to form a polymerase-nucleic acid complex, the binding of a nucleotide to the polymerase-nucleic acid complex to form an open polymerase-nucleic acid-nucleotide ternary complex, the transition of the polymerase in the open polymerase-nucleic acid-nucleotide ternary complex to the closed polymerase'-nucleic acid-nucleotide ternary complex, catalytic bond formation between the nucleotide and nucleic acid in the closed polymerase'-nucleic acid-nucleotide ternary complex to form a closed polymerase'-extended nucleic acid-pyrophosphate complex, transition of the closed polymerase'-extended nucleic acid-pyrophosphate complex to an open polymerase-extended nucleic acid-pyrophosphate complex, release of pyrophosphate from the open polymerase-extended nucleic acid-pyrophosphate complex to form an open polymerase-extended nucleic acid complex, and eventual (i.e. optionally after several repetitions of nucleotide binding incorporation) release of the extended nucleic acid from the open polymerase-extended nucleic acid complex to form the uncomplexed polymerase. One or more of the transitions that a polymerase undergoes when adding a nucleotide to a nucleic acid can be detected using a conformationally labeled polymerase. Similarly, the reverse transitions can be detected using a conformationally labeled polymerase, for example, to detect one or more transitions that occur when a nucleotide is removed from a nucleic acid during pyrophosphorolysis or hydrolysis. For example, time based or kinetic measurement of signals arising from a conformationally labeled polymerase can be used to distinguish one transition from another.

In particular embodiments, time based or kinetic measurements of a conformationally labeled polymerase can be used to distinguish the species of nucleotide that is added to a nucleic acid. For example, a time based or kinetic measurement can be used to distinguish the species of nucleotide that is bound to a polymerase to form a polymerase-nucleic acid-nucleotide complex, to distinguish the species of nucleotide that is involved in the transition of a polymerase in a polymerase-nucleic acid-nucleotide complex to a polymerase'-nucleic acid-nucleotide complex, to distinguish the species of nucleotide that is involved in catalytic bond formation between the nucleotide and a nucleic acid in a polymerase'-nucleic acid-nucleotide complex to form a polymerase'-extended nucleic acid-pyrophosphate complex, to distinguish the species of nucleotide that is involved in transition of a polymerase'-extended nucleic acid-pyrophosphate complex to a polymerase-extended nucleic acid-pyrophosphate complex, or to distinguish the species of nucleotide that is involved in release of pyrophosphate from a polymerase-extended nucleic acid-pyrophosphate complex to form a polymerase-extended nucleic acid complex. Alternatively or additionally, time based or kinetic measurements of a conformationally labeled polymerase can be used to distinguish the binding and/or incorporation of a correctly Watson-Crick base-paired nucleotide from one that is incorrectly base-paired to the template nucleic acid. Similarly, the binding and/or incorporation of a methylated nucleotide can be distinguished from one that is not methylated, or the binding and/or incorporation of a ribonucleotide can be distinguished from a deoxyribonucleotide.

A sequence of time based or kinetic measurements for a conformationally labeled polymerase can be used to determine the sequence of a template nucleic acid being used by the polymerase to synthesize a complementary strand. It will be understood that the sequence of the template strand can be inferred from the sequence of nucleotides incorporated into the strand that is being extended. As such, determination of the sequence of one strand will be understood to include determination of the sequence of its complementary strand.

Similarly, time based or kinetic measurements of a conformationally labeled polymerase can be used to distinguish the species of nucleotide that is removed from a nucleic acid. For example, a time based or kinetic measurement can be used to distinguish the species of nucleotide that is bound to a polymerase to form the intermediates set forth above (albeit in the reverse direction from that exemplified above for nucleotide addition) and shown in FIG. 2. A sequence of time based or kinetic measurements for a conformationally labeled polymerase can be used to determine the sequence of a template nucleic acid that is hybridized to a strand being degraded by the polymerase.

The time duration of a single nucleotide's binding and incorporation by a polymerase can be at least 10 ms, 20 ms, 50 ms, 100 ms, 1000 ms, 5000 ms, 10,000 ms, 60,000 ms or longer. Any of a variety of detection techniques known in the art can be used including, but not limited to, rapid kinetics analysis including stopped-flow and quench flow techniques, CCD-based detection systems, EMCCD-based detection systems, ICCD-based detection systems, total internal reflectance fluorescence (TIRF)-based systems, or CMOS-based detection systems.

Detection can be carried out at ensemble or single molecule levels in real time. Ensemble level detection includes detection that occurs in a way that a population of molecules is detected such that individual molecules in the population are not distinguished from each other. Thus, ensemble detection provides an average signal from the molecules in the population. The population can be a colony or feature on a solid support such as an array. The molecules in the population typically share common characteristics, for example, a common sequence shared by several nucleic acid molecules. In particular embodiments, ensemble detection utilizes nucleotide analogs having reversible blocking groups as set forth in further detail below. At the ensemble level, the base calling can be achieved by cycling one or two types of nucleotides each time.

Detection at a single molecule level includes detection that occurs in a way that an individual molecule is distinguished. Thus, single molecule detection provides a signal from an individual molecule that is distinguished from one or more signals that may arise from a population of molecules within which the individual molecule is present.

Any of a variety of nucleotide species can be useful in a method or composition set forth herein. For example, naturally occurring nucleotides can be used such as ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Typically, dNTP nucleotides are incorporated into a DNA strand by DNA polymerases and NTP nucleotides are incorporated into an RNA strand by RNA polymerases. In particular embodiments, NTP nucleotides or analogs thereof can be incorporated into DNA by a DNA polymerase, for example, in cases where the NTP, or analog thereof, is capable of being incorporated into the DNA by the DNA polymerase and where the rate or time duration for a DNA polymerase transition using the NTP, or analog thereof, can be distinguished from the rate or time duration for the DNA polymerase transition using another nucleotide. Alternatively, dNTP nucleotides or analogs thereof can be incorporated into RNA by an RNA polymerase, for example, in cases where the dNTP, or analog thereof, is capable of being incorporated into the RNA by the RNA polymerase and where the rate or time duration for an RNA polymerase transition using the dNTP, or analog thereof, can be distinguished from the rate or time duration for the RNA polymerase transition using another nucleotide. Additionally, dNTP nucleotides or analogs thereof can be incorporated into DNA from an RNA template by a reverse transcriptase, for example, in cases where the dNTP, or analog thereof, is capable of being incorporated into the DNA from an RNA template by a reverse transcriptase and where the rate or time duration for a reverse transcriptase transition using the dNTP, or analog thereof, can be distinguished from the rate or time duration for the reverse transcriptase transition using another nucleotide. The relative difference in rate or time duration can be a relative increase in the rate, a relative increase in duration, a relative decrease in rate or a relative decrease in duration. The relative difference in intensity or other properties of probes, such as fluorescence correlation or polarization, at the end point of the duration can also be used to distinguish different nucleotides. Additionally, the same principle can be applied to distinguish methylated nucleotides in the template based on the relative difference in rate or time duration or intensity or other properties at the end point of the duration for a DNA polymerase incorporating a nucleotide opposite the methylated nucleotide in the template.

Non-natural nucleotide analogs are also useful. Particularly useful non-natural nucleotide analogs include, but are not limited to, those that produce a detectably different rate or time duration for a polymerase transition that can be distinguished from the rate or time duration for a polymerase transition with another nucleotide. For example, a non-natural nucleotide analog may usefully produce a detectably different rate or time duration for a polymerase transition that can be distinguished from the rate or time duration for the same transition of the polymerase with another nucleotide such as a naturally occurring nucleotide. Exemplary nucleotide analogs that can be used include, but are not limited to, dNTPαS; NTPαS; nucleotides having unnatural nucleobases identified in Hwang et al, *Nucl. Acids Res.* 34:2037-2045 (2006) (incorporated herein by reference) as ICS, 3MN, 7AI, BEN, DM5, TM, 2Br, 3Br, 4Br, 2CN, 3CN, 4CN, 2FB, 3FB, MM1, MM2 and MM3; or nucleotides having other non-natural nucleobases such as those described in Patro et al. *Biochem.* 48:180-189 (2009) (incorporated herein by reference) which include 2-amino-1-deazapurine, 1-deazapurine, 2-pyridine, hypoxanthine, purine, 6-Cl-purine, 2-amino-dA, 2-amino purine or 6-Cl-2-amino-purine or nucleotides having non-natural nucleobases such as those described in Krueger et al. *Chem Biol.* 16:242-8 (2009) (incorporated herein by reference) which include iso-G, iso-C, 5SICS, MMO2, Ds, Pa, FI, FB, dZ, DNB, thymine isosteres, 5-NI, dP, azole-carboxamide, xA, Im-No, Im-ON, J, A*, T*.

Non-natural nucleotide analogs having 5' modifications are particularly useful. The non-natural nucleotide analog will typically have a triphosphate but can have more or fewer phosphates as set forth elsewhere herein. In particular embodiments, one or more of the alpha phosphate, beta phosphate or gamma phosphate of a non-natural nucleotide is covalently attached to a moiety other than oxygen. A moiety that is attached to a phosphate or otherwise present at the 5' position can provide a negative charge, a positive charge, metal-chelating activity or steric bulk. Exemplary moieties include, but are not limited to, amino acids, in the L-enantiomer form or R-enantiomer form, such as histidine, aspartate, glutamate, tryptophan, phenylalanine, methionine, tyrosine, cysteine, glycine alanine, or proline; an amino group; a chelated metal such as magnesium or manganese; a methyl group; a halogen such as bromine, chlorine or iodine; a thiol group; an electron withdrawing group; an electron donating group; an aromatic amine; or an aliphatic amine. These and other moieties may be advantageous in embodiments where they provide an interaction with a polymerase, or other nucleic acid enzyme, that differs from the interaction that the enzyme has with a nucleotide lacking the moiety. As such, the presence and absence of the moiety on respective nucleotide species can be exploited to distinguish the nucleotide species in a sequencing method, for example, based on the rate, time duration and/or intensity for a conformational signal change in a nucleic acid enzyme acting on the nucleotide species. See Example V below.

Figure 4:
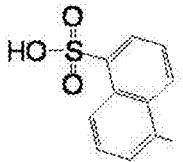
FIG. 4 shows exemplary moieties that can be attached to a nucleotide via a gamma-phosphoamidite linker.

FIG. 3 provides further examples of non-natural nucleotide triphosphates that can be included in a composition set forth herein or used in a method set forth herein. The examples shown in the figure contain a deoxyribose sugar moiety having a hydroxyl at the 3' position. It will be understood that the 3' position can have a terminating group, reversible terminating group or other moiety such as those set forth elsewhere herein or otherwise known in the art. Furthermore other sugar moieties can be used such as ribose or analogs known in the art. The "Base" moiety can be any of a variety of bases known in the art including, without limitation, adenine, thymine, uracil, cytosine, guanine or analogs thereof. As shown in the figure exemplary triphosphate moieties include, but are not limited to, alpha-boranotriphosphate (FIG. 3A); alpha-phosphorothioate (FIG. 3B); beta,gamma-halomethylene bridged triphosphate (FIG. 3C) and gamma-phosphoamidate modified triphosphates (FIG. 3D). Exemplary R groups that can be present in the gamma-phosphoamidate modified triphosphates are shown in FIG. 4, wherein the "N—" moiety represents the linkage to the gamma phosphate. As shown in FIG. 4 the R group can be, for example, an electron withdrawing group, electron donating group, aromatic amine, aliphatic amine or other moiety. Exemplary gamma phosphoamidate-linked moieties and methods for their synthesis are described in Mulder et al., *Nucleic Acids Res.* 33:4865-4873 (2005) and Berde et al., *J. Biol. Chem.* 254:12069-12073 (1979), each of which is incorporated herein by reference. Other examples of nucleotides having a moiety other than oxygen attached to a triphosphate moiety include those having 1-alpha-thiol phosphate or 1-alpha-borano phosphate as further described in Example III.

Another useful type of nucleotide is a caged nucleotide. An exemplary caged nucleotide has a moiety with a photo-isomerizable double bond. In particular embodiments, a first isomer of the caged nucleotide has a different rate or time duration for a conformational signal change of a polymerase than a second isomer of the caged nucleotide. For example, the first isomer may readily bind to the polymerase and be incorporated into a nucleic acid under particular conditions whereas the second isomer will not appreciably bind to the polymerase and/or be incorporated into the nucleic acid under the particular conditions. Azobenzene is a moiety that undergoes photo-isomerization whereby UV radiation causes trans to cis conversion and blue light causes cis to trans conversion. Other moieties that undergo photo-isomerization and conditions for their photo-isomerization are known in the art and include, for example, stilbene, and cinnamic acid.

A further example of a caged nucleotide is one having a moiety that is photo-cleavable. In some embodiments, the presence of the moiety on the nucleotide alters (e.g. reduces or increases) the rate or time duration for a conformational signal change of a polymerase compared to the nucleotide without the moiety. For example, a nucleotide lacking the moiety may readily bind to a polymerase and be incorporated into a nucleic acid under particular conditions whereas the presence of the moiety will reduce or prevent binding to the polymerase and/or incorporation into the nucleic acid under the particular conditions. Exemplary photo-cleavable moieties include, but are not limited to (1-(4,5-dimethoxy-2-nitrophenyl)ethyl) ester (i.e. DMNPE) and (1-(2-nitrophenyl) ethyl) ester (i.e. NPE). See *Meth. Enzymol.* 291:307-347 (1998), which is incorporated herein by reference.

A photo-isomerizable moiety or photo-cleavable moiety can be attached to a nucleotide at any of a variety of locations in the nucleotide including, but not limited to, the ribose moiety, a phosphate moiety, or a base moiety or other specific locations exemplified herein in the context of other nucleotide analogs. Furthermore, a photo-isomerizable moiety or photo-cleavable moiety can be attached to one or more nucleotide species used in a method or reaction set forth herein. For example, such moieties can be present on a nucleotide analog having a base that pairs with adenine, thymine, guanine or cytosine. Mixtures of nucleotides can be used that have different photo-isomerizable or photo-cleavable moieties. The different moieties can be tuned for photoreactions with different wavelengths of light. As such, individual nucleotide types can be activated (or deactivated) using different wavelengths of light in order to provide light-gated control of individual nucleotide types in a reaction such as a sequencing reaction set forth herein.

Use of one or more caged nucleotide species can provide a means to initiate, modulate or attenuate a reaction set forth herein. For example, one or more photo-isomerizable or photo-cleavable nucleotide species can be introduced to a reaction in an inactive conformation and subsequently light activation can be used to initiate binding of nucleotides to a polymerase or addition of the nucleotides to a nucleic acid by a polymerase. Thus, light activation can provide temporal control of the start point for a reaction set forth herein. Alternatively or additionally, photo-isomerizable nucleotides that are in an active conformation can be inactivated by light to pause or stop a polymerization reaction. Stopping a reaction can be achieved by separating reaction components from each other, for example by washing the nucleotides away from a solid-phase attached nucleic acid. Such a separation step need not be carried out and instead the reaction can be resumed by toggling the photo-isomerizable nucleotide to an active form to resume polymerization. As such, caged nucleotides provide a means to achieve light-gated control of a variety of reactions such as the sequencing methods set forth herein.

Light-gating is particularly useful for embodiments that use real-time detection at a single molecule level. Single molecule reactions are stochastic by nature. Light-gating provides for temporal control of detection to coincide with initiation of the single molecule reaction thereby providing more accurate detection.

Although an advantage of light-gating is set forth above in regard to real-time detection at a single molecule level, it will be understood that light gating is also useful for ensemble-level detection. For example, whether used for a single-molecule or ensemble level embodiments, light gating can provide spatial control of a reaction. More specifically, a sample can contain a relatively large pool of nucleotides and focused light can be delivered to a portion of a sample to activate a sub-population of the nucleotides. Thus, repeated activation of a subpopulation of nucleotides can be used instead of repeated fluidic delivery steps.

Variants of polymerase can be engineered to incorporate and extend natural or non-natural nucleotides at an appropriate or otherwise desired speed to allow detection of differences in rate or time duration when different nucleotides are incorporated and extended.

A reaction composition or method can include one or more nucleotide species. For example, a reaction composition or method used for sequence analysis can include four different nucleotide species capable of forming Watson-Crick base pairs with four respective nucleotide species in a nucleic acid template being synthesized. Particular embodiments can include at least two different nucleotide species, at least three different nucleotide species, at least four different nucleotide species, or more. At least two of the nucleotide species can be non-natural nucleotide analogs, at least three of the nucleotide species can be non-natural nucleotide analogs, or at least four of the nucleotide species can be non-natural nucleotide analogs. Thus a reaction composition or method can include a mixture of natural nucleotides and non-natural nucleotide analogs. Alternatively, a reaction composition can lack natural nucleotides having instead only non-natural nucleotide analogs. The reaction can be carried out under conditions in which only non-natural nucleotide analogs are incorporated into a growing nucleic acid by a polymerase or other nucleic acid enzyme.

In some embodiments, a reaction composition or method can include nucleotide species that base-pair with no more than one nucleotide species in a nucleic acid template. For example, a method can be carried out under conditions wherein different nucleotide species are contacted with a polymerase and nucleic acid in separate, sequential reactions. Specifically, a nucleotide species that base-pairs with A can be added in a first reaction, a nucleotide species that base-pairs with C can be added in a second reaction, a nucleotide species that base-pairs with T can be added in a third reaction, and a nucleotide species that base-pairs with G can be added in a fourth reaction. The reactions are referred to as first, second, third and fourth merely to illustrate that the reactions are separate but this does not necessarily limit the order by which the species can added in a method set forth herein. Rather, nucleotide species that base-pair with A, C, T or G can be added in any order desired or appropriate for a particular embodiment of the methods. Typically in a sequencing method nucleotide species that base-pair with four different nucleotide species in a given template nucleic acid are added sequentially to complete a cycle of the sequencing method. However, it will be understood that fewer than four nucleotide additions can be used in some embodiments. Furthermore, it will be understood that mixtures of nucleotides that base-pair with more than one but no more than 2, 3 or 4 nucleotide species can be used. Similarly, mixtures of nucleotides that base-pair with more than two but no more than 3 or 4 nucleotide species can be used. Or mixtures of nucleotides that base-pair with more than three but no more than 4 nucleotide species can be used.

In particular embodiments, a method set forth herein can be carried out under conditions wherein one or more of the nucleotides lack detectable probes. A method can be carried out under conditions wherein all of the nucleotides lack detectable probes. For example, the nucleotide(s) can lack an exogenous probe. Exogenous probes include any probes that are not present in the structure of a natural nucleotide including, for example, an optical probe such as a fluorophore, optical quencher, or chromophore.

In particular embodiments, a method set forth herein can be carried out under conditions wherein one or more of the nucleotides lack quenchers. A method can be carried out under conditions wherein all of the nucleotides lack quenchers. For example, the nucleotide(s) can lack quenchers that interact with a probe that is detected, such as a probe on a conformationally labeled enzyme or on a nucleic acid. Exemplary quenchers include optical quenchers such as those that prevent or reduce detectable emission from a nearby fluorophore.

In particular embodiments, a method set forth herein can be carried out under conditions wherein a nucleic acid, whether a template strand or its complement, lacks detectable probes. For example, a nucleic acid can lack an exogenous probe, such as those set forth above. Similarly, a method set forth herein can be carried out under conditions wherein the nucleic acid lacks quenchers. For example, the nucleic acid can lack quenchers that interact with a probe that is detected such as a probe on a conformationally labeled enzyme or on a nucleotide.

In some embodiments, a method can be carried out under conditions wherein at least one nucleotide is undetectable including, for example, a condition wherein all of the nucleotides are undetectable. Alternatively or additionally, a method can be carried out under conditions wherein a nucleic acid, whether a template strand or its complement, is undetectable. A nucleotide or nucleic acid can be undetectable due to the use of a detection device or detection mode that is incapable of detecting signals produced by the nucleotides or nucleic acids. For example, an optical device can include an optical filter that rejects optical signals in a range produced by the nucleotides and/or nucleic acids. Alternatively or additionally, an optical device can be configured such that it does not substantially excite nucleotides and/or nucleic acids in a way that optically detectable signals are produced.

A method set forth herein can be carried out in solution or on a solid support. A solution-phase method will be understood to be one where all components that participate in a reaction are in solution, the components including, for example, a nucleic acid, nucleic acid enzyme and nucleotide. A solid-phase reaction is one where one or more of the components occur in or on a solid support. For example, a nucleic acid, nucleic acid enzyme or nucleotide can be in or on a solid support during the course of a solid-phase reaction. A nucleic acid that is attached to the solid support can be a template nucleic acid such as one that is copied by a polymerase, a primer nucleic acid such as one that is extended by a polymerase, or a double stranded nucleic acid such as one that is acted upon by a polymerase, exonuclease or other nucleic acid enzyme.

Any of a variety of solid-support materials can be used in a method or composition set forth herein. Useful materials include, for example, those that are separable from each other such as beads, particles, microspheres, or chromatographic supports; and those that form a continuous material such as a flow cell, microchip or other chip, microscope slide or other planar surface, or the like. Particularly useful supports are those used for microarrays. Useful materials for a microarray or other solid support include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful substrates include those that allow optical detection, for example, by being translucent to energy of a desired detection wavelength and/or do not produce appreciable background fluorescence at a particular detection wavelength.

A reaction component can be attached to a solid support by methods known in the art. In some embodiments, a component such as a nucleic acid can be synthesized on a solid support by sequential addition of nucleotide units directly on the solid support. Methods known in the art for synthesis of a variety of nucleic acids on solid supports can be used. Alternatively, components can be synthesized or otherwise obtained first, and then covalently attached to a solid support. The components can be attached to functional groups on a solid support. Functionalized solid supports can be produced by methods known in the art and, if desired, obtained from any of several commercial suppliers for beads and other supports having surface chemistries that facilitate the attachment of a desired functionality by a user. Exemplary surface chemistries that are useful in the invention include, but are not limited to, amino groups such as aliphatic and aromatic amines, carboxylic acids, aldehydes, amides, chloromethyl groups, hydrazide, hydroxyl groups, sulfonates or sulfates. If desired, a component can be attached to a solid support via a chemical linker. Such a linker can have characteristics that provide, for example, stable attachment, reversible attachment, sufficient flexibility to allow desired interaction with another reaction component, or to avoid undesirable binding reactions. By way of example, a surface with an array of attached oligo dT molecules can be used to immobilize sheared genomic DNA pieces that have poly A tail transferred by Terminal transferase. Further exemplary methods that can be used in the invention to attach polymer probes to a solid support are described in Pease et al., *Proc. Natl. Acad. Sci. USA* 91(11): 5022-5026 (1994); Khrapko et al., *Mol Biol (Mosk) (USSR)* 25:718-730 (1991); Stimpson et al., *Proc. Natl. Acad. Sci. USA* 92:6379-6383 (1995) or Guo et al., *Nucleic Acids Res.* 22:5456-5465 (1994), each of which is incorporated herein by reference.

A reaction component can be attached to a support in a way that provides detection at a single molecule level or at an ensemble level. For example, a population of nucleic acids can be attached to a solid support in a way that conformationally labeled polymerases that interact with individual nucleic acid molecules in the population can be distinguished from conformationally labeled polymerases that interact with other nucleic acid molecules on the support. Single molecule detection can also be achieved with a population of conformationally labeled polymerases that is attached to a solid support in a way that signals arising from a particular polymerase can be distinguished from signals arising from other polymerases on the support. Reaction components can be separated from each other on a solid support due to surface features or contours such as those that form wells, posts, channels or the like. Alternatively or additionally, separation can be achieved by providing spacing between molecules that is greater than the resolution of a particular detection device that is in use.

Ensemble detection can be achieved for reaction components that are attached to a surface to form colonies or clusters for ensemble detection. For example, one or more colonies each containing several conformationally labeled polymerases can be attached to a surface. Colonies of nucleic acids can be attached to a surface using methods known in the art such as bridge amplification or emulsion PCR. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, as described in Lizardi et al., *Nat. Genet.* 19:225-232 (1998) and US 2007/0099208 A1, each of which is incorporated herein by reference. Exemplary emulsion PCR methods are described in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference in its entirety.

Whether occurring in solution phase or solid phase formats, a polymerase extension method can be carried out by a single delivery of nucleotides or by multiple deliveries of nucleotides. In an exemplary embodiment, the former configuration can include a single delivery of several different species of nucleotides such that the polymerase is able to add several nucleotides to a growing nucleic acid strand. In such a method multiple nucleotide deliveries are not necessary to achieve extension of a primer by at least 2, 3, 5, 10, 50, 100, 250, 500, 1000, 10000 or more nucleotides. Typically, four different nucleotide species will be delivered, but if desired, fewer than four can be delivered. Delivering nucleotides one at a time is one way for base calling at the ensemble level.

In a particular embodiment, one or more blocked nucleotide species can be delivered such that single base extension occurs. In an exemplary embodiment of the multiple nucleotide addition format, reversibly blocked nucleotides can be delivered each time. Deblocking and washing steps can be carried out between nucleotide addition steps. Typically a chemically reactive deblocking group is used; however a photo-sensitive block can be used for fast deblocking by light. Exemplary modifications that can be used to render a nucleotide reversibly blocked and steps that can be used for cyclical addition of blocked nucleotides by polymerase extension are described in U.S. Pat. Nos. 7,427,673; 7,414,116; and 7,057,026 and PCT publications WO 91/06678 and WO 07/123744, each of which is incorporated herein by reference.

Reversibly blocked nucleotides can be particularly useful for detection at an ensemble level. The blocking group on the nucleotide can provide quantization or synchronization of extension events occurring for a population of conformationally labeled polymerases. An example is illustrative as follows. A solid support is provided having a cluster of identical nucleic acids having a common template sequence. Conformationally labeled polymerases are bound to templates to form polymerase-template species in the cluster. Reversibly blocked nucleotides of a particular type (e.g. A, C, T or G) are delivered to the cluster of polymerase-template species thereby resulting in a single extension for each species in the cluster. The extension event at each cluster is detected as an average signal from the conformationally labeled polymerases in the cluster. Following the detection event, the reversible blocking groups are removed from the nucleotides that were incorporated into the cluster and then the nucleotide delivery and detection events are repeated. In this way, the extension events occurring for several template-polymerase species in the cluster are synchronized or quantized with respect to each nucleotide addition event. As such the sequence of signals from the cluster can be detected in order to determine the template sequence for the nucleic acids of the cluster. Reversibly blocked nucleotides are also useful for embodiments that employ detection at single molecule resolution. As such, the method steps exemplified above are not intended to be limited to ensemble-based detection.

Also provided herein is a method of determining a sequence of nucleotides for a nucleic acid template. The method can include the steps of contacting the nucleic acid template with a conformationally labeled exonuclease under conditions wherein the conformationally labeled exonuclease catalyzes sequential removal of nucleotide species from the nucleic acid template, wherein the sequential removal of each different nucleotide species produces a conformational signal change from the conformationally labeled exonuclease and wherein the rate or time duration for the conformational signal change is distinguishable for each different nucleotide species that is removed; detecting a series of changes in the signal from the conformationally labeled exonuclease under the conditions; and determining the rates or time durations for the changes in the signal for the series of changes in the signal from the conformationally labeled exonuclease, thereby determining the sequence of nucleotides for the nucleic acid template. The conformationally labeled exonuclease can be a polymerase having exonucleolytic or pyrophosphorolysis activity.

In particular embodiments, a nucleic acid that is sequenced using a conformationally labeled exonuclease can contain one or more species of modified nucleotide subunits. Individual species of nucleotide subunits can contain a unique moiety that interacts with an exonuclease during removal from the nucleic acid to produce a rate or time duration for a conformational signal change that is distinguishable from the rate or time duration produced by the other types of nucleotide species that are removed from the nucleic acid. The nucleic acid can contain at least 1, at least 2, at least 3 or at least 4 modified nucleotide species. Exemplary species include those having modified alpha-phosphate moieties such as those set forth above, shown in FIGS. 3 and 4 or otherwise known in the art.

This disclosure further provides a method of determining a sequence of nucleotides for a nucleic acid template. The method can include the steps of contacting the nucleic acid template with a conformationally labeled polymerase and at least four different nucleotide species under conditions wherein the conformationally labeled polymerase catalyzes sequential addition of the nucleotide species to form a nucleic acid complement of the nucleic acid template, wherein the sequential addition of each different nucleotide species produces a conformational signal change from the conformationally labeled polymerase and wherein the rate or time duration for the conformational signal change is distinguishable for each different nucleotide species; detecting a series of changes in the signal from the conformationally labeled polymerase under the conditions; determining the rates or time durations for the changes in the signal, thereby determining the sequence of nucleotides for the nucleic acid template; contacting the nucleic acid template with a conformationally labeled exonuclease under conditions wherein the conformationally labeled exonuclease catalyzes sequential removal of nucleotide species from the nucleic acid template, wherein the sequential removal of each different nucleotide species produces a conformational signal change from the conformationally labeled exonuclease and wherein the rate or time duration for the conformational signal change is distinguishable for each different nucleotide species that is removed; detecting a series of changes in the signal from the conformationally labeled exonuclease under the conditions; and determining the rates or time durations for the changes in the signal for the series of changes in the signal from the conformationally labeled exonuclease.

The conformationally labeled polymerase and the conformationally labeled exonuclease can be the same molecular species or different molecular species. The species can differ from each other, for example, in their primary amino acid sequences, the location of one or more labels, the chemical structure of one or more labels, the presence or absence of a protein domain (such as an exonuclease domain), or the presence or absence of a modification that substantially influences exonuclease or polymerase activity.

A method of sequencing a nucleic acid can include a polymerase phase for sequencing-by-synthesis of the nucleic acid followed by an exonuclease phase for sequencing-by-degradation of the nucleic acid. The degradation phase can advantageously provide a proofreading function for the synthesis phase. In proofreading embodiments, the exonuclease phase can provide a resolution that is equivalent to or lower than the resolution of the polymerase phase. For example, a sequencing-by-synthesis phase that uses a conformationally labeled polymerase can be used to obtain a single nucleic acid sequence that resolves the positions of all four nucleotide species and a subsequent sequencing-by-degradation phase can be used to determine the locations of at most 1, 2 or 3 of the four nucleotide species. Proofreading can be achieved by aligning the locations of the nucleotide species identified in the sequencing-by-degradation phase with their locations as identified in the sequencing-by-synthesis phase, whereby any misalignment would indicate a potential error in the sequence obtained in the sequencing-by-synthesis phase.

For proofreading embodiments, a sequencing-by-synthesis phase that incorporates a nucleotide species having a modified alpha-phosphate moiety is particularly useful because the modified alpha-phosphate moiety if present in the synthesized nucleic acid can provide a rate or time duration for the conformational signal change that is distinguishable from that produced by other nucleotide units in the nucleic acid. Accordingly, it can be advantageous to include at least one modified alpha-phosphate moiety in a method of sequencing. It can be further advantageous to include no more than 2 or 3 nucleotides having the modified alpha-phosphate moiety, for example, to allow the nucleotide having the modified alpha-phosphate moiety to be distinguished from other nucleotides in a proofreading embodiment.

In a further embodiment a method of determining a sequence of nucleotides for a nucleic acid sample is provided. The method can include the steps of providing an array of nucleic acid templates, wherein the nucleic acid templates include nucleotide sequence fragments of the nucleic acid sample; contacting the array of nucleic acid templates with conformationally labeled polymerases and at least four different nucleotide species under conditions wherein the conformationally labeled polymerases catalyze sequential addition of the nucleotide species to form nucleic acid complements of the nucleic acid templates, wherein the sequential addition of each different nucleotide species produces a conformational signal change from the conformationally labeled polymerase and wherein the rate or time duration for the conformational signal change is distinguishable for each different nucleotide species; detecting a series of changes in the signal from the conformationally labeled polymerase under the conditions and at individual locations of the array; and determining the rates or time durations for the changes in the signal at the individual locations of the array, thereby determining the sequence of nucleotides for the nucleic acid sample.

Multiplex detection can be achieved using a microarray format. Examples of array formats that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897, each of which is incorporated herein by reference. Other useful array formats are those in which separate substrates are located in solution or on a surface including, without limitation, those having beads as described, for example, in U.S. Pat. Nos. 6,023,540, 6,200,737, 6,327,410 and 6,355,431; US Pat. Pub. No. 2002/0102578; and PCT publications WO 98/40726, WO 98/50782, WO 99/18434 and WO 00/63437, each of which is incorporated herein by reference. For embodiments including bead-based arrays, the arrays can be made, for example, by adding a solution or slurry of the beads to a substrate containing attachment sites for the beads. Beads can be loaded into the wells of a substrate, for example, by applying energy such as pressure, agitation or vibration, to the beads in the presence of the wells. Methods for loading beads onto array substrates that can be used in the invention are described, for example, in U.S. Pat. No. 6,355,431, which is incorporated herein by reference.

A useful method for making arrays is photolithography-based polymer synthesis. For example, Affymetrix™ GeneChip™ arrays can be synthesized in accordance with techniques sometimes referred to as VLSIPS™ (Very Large Scale Immobilized Polymer Synthesis) technologies. Some aspects of VLSIPS™ and other microarray manufacturing methods and techniques have been described in U.S. Pat. Nos. 5,143,854, 5,242,974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752, each of which is incorporated herein by reference.

A spotted array can also be used. An exemplary spotted array is a CodeLink™ Array available from Amersham Biosciences. CodeLink™ Activated Slides are coated with a long-chain, hydrophilic polymer containing amine-reactive groups. This polymer is covalently cross-linked to itself and to the surface of the slide. Attachment of reaction components can be accomplished through covalent interaction between the amine-modified nucleic acid or protein and the amine reactive groups present in the polymer. Components can be attached at discrete locations using spotting pens. Another array that is useful in the invention can also be manufactured using inkjet printing methods such as SurePrint™ Technology available from Agilent Technologies. Such methods can be used to synthesize nucleic acids in situ or to attach pre-synthesized reaction components having moieties that are reactive with a substrate surface.

The size of an array can vary depending on the desired use of the array. Arrays useful in the invention can have complexity that ranges from about 2 different reaction sites to many millions, billions or higher. The density of an array can be from 2 to as many as a billion or more different reaction sites per square cm. Very high density arrays are useful in the invention including, for example, those having at least about 10,000,000 reaction sites/cm$^2$, including, for example, at least about 100,000,000 reaction sites/cm$^2$, 1,000,000,000 reaction sites/cm$^2$, up to about 2,000,000,000 reaction sites/cm$^2$ or higher. High density arrays can also be used including, for example, those in the range from about 100,000 reaction sites/cm$^2$ to about 10,000,000 reaction sites/cm$^2$. Moderate density arrays useful in the invention can range from about 10,000 reaction sites/cm$^2$ to about 100,000 reaction sites/cm$^2$ Low density arrays are generally less than about 10,000 reaction sites/cm$^2$.

A method of determining a sequence of nucleotides for a nucleic acid (i.e. a nucleic acid sequencing method) can be carried out using a variety of protocols. Typically, a nucleic acid sequencing method is cyclic due to repetitious addition of nucleotide or oligonucleotide units to a growing nucleic acid polymer or repetitious removal of nucleotide or oligonucleotide units from a nucleic acid polymer. A nucleic acid sequencing protocol can also, but need not, include repeated cycles of manipulation, each cycle of manipulations including one or more steps. For example, each cycle of manipulations can include one or more steps that result in detection of a single nucleotide that is added to a growing nucleic acid. Sequencing methods that utilize a conformationally labeled polymerase and reversible terminators generally provide for detection of a single nucleotide per cycle. Similarly, each cycle of manipulations can include one or more steps that result in detection of a single nucleotide that is removed from a shrinking (or fragmenting) nucleic acid. Alternatively, some protocols provide detection of multiple nucleotides per cycle, for example, by exploiting the cyclic nature of nucleic acid enzymes and detection of their activity. In some embodiments, this detection of multiple nucleotides is carried out using real-time detection of conformational signal changes following a single fluidic manipulation. Several exemplary sequencing protocols are set forth below for illustration.

A first exemplary nucleic acid sequencing protocol can be carried out for a sequencing reaction that includes, inter alia, a primed nucleic acid template, conformationally labeled polymerase and a set of four different nucleotide species. The four different nucleotide species differ in their base composition and in the rate or time duration for a conformational signal change that occurs for the polymerase when each species is incorporated into the primed nucleic acid template. The four different nucleotide species are extendable, for example, lacking terminator groups at the 3' position of the ribose moiety. The protocol can include delivery of all four nucleotides to the sequencing reaction such that the four nucleotides are present simultaneously and real time detection of the conformational signal changes occurring in the polymerase, whereby the identity of each nucleotide species is distinguished according to the rate or time duration for the respective conformational signal change. A single nucleic acid sequence that resolves the positions of all four nucleotide species can be obtained using the first exemplary protocol.

A second exemplary nucleic acid sequencing protocol can be carried out for a sequencing reaction that includes, inter alia, a primed nucleic acid template, conformationally labeled polymerase and a set of four different nucleotide species. The four different nucleotide species differ in their base composition. A first nucleotide of the set differs from the other three nucleotides in the rate or time duration for a conformational signal change that occurs for the polymerase when the first nucleotide is incorporated into the primed nucleic acid template. The other three nucleotides are not necessarily distinguished from each other based on the rate or time duration for a conformational signal change that occurs for the polymerase when they are incorporated into the primed nucleic acid template. The four different nucleotide species are extendable, for example, lacking terminator groups at the 3' position of the ribose moiety. The protocol can include delivery of all four nucleotides to the sequencing reaction such that the four nucleotides are present simultaneously and real time detection of the conformational signal changes occurring in the polymerase, whereby the identity of the first nucleotide species is distinguished according to the rate or time duration for the respective conformational signal change and whereby incorporation of the other three nucleotides is detected based on the conformational signal change. A single nucleic acid sequence that resolves the positions of a single nucleotide species can be obtained using the second exemplary protocol.

A third exemplary nucleic acid sequencing protocol can be carried out as set forth above for the second exemplary nucleic acid sequencing protocol with the exception that a second set of nucleotides is used in place of the first set of nucleotides that was used in the second exemplary protocol. The second set of nucleotides can differ from the first set of nucleotides in the identity of the nucleotide that differs from the other three nucleotides in the rate or time duration for the conformational signal change. For example, the second set of nucleotides can include dATP, dTTP, dCTP and γANSdGTP whereas the first set of nucleotides included dATP, dTTP, γANSdCTP and dGTP. Again a single nucleic acid sequence that resolves the positions of a single nucleotide species (i.e. cytosine) can be obtained using the third exemplary protocol. Comparison of the results of the second and third sequencing protocol can provide a low resolution sequence of the nucleic acid template in which the position of two nucleotides (i.e. guanine and cytosine) is resolved.

A low resolution sequence can provide a useful scaffold for sequence alignment as set forth in U.S. Patent Publ. Nos. 2010/0173303 and 2010/0279882, each of which is incorporated herein by reference. Alternatively, the third exemplary nucleic acid sequencing protocol can be repeated using a third and fourth set of nucleotides whereby two different nucleotides are respectively distinguishable. Comparing the results of all four sequencing protocols can provide a single nucleic acid sequence that resolves the positions of all four nucleotide species in the nucleic acid template. In some embodiments only three of the above protocols need be run such that the locations of 3 types of bases are detected. In this scenario, the location of the fourth type of base can be inferred from the data derived for the other 3 types of bases.

A fourth exemplary nucleic acid sequencing protocol can be carried out for a sequencing reaction that includes, inter alia, a primed nucleic acid template, conformationally labeled polymerase and a set of four different nucleotide species, wherein each nucleotide species has a reversible terminator moiety. The four different nucleotide species differ in their base composition and in the rate or time duration for a conformational signal change that occurs for the polymerase when each species is incorporated into the primed nucleic acid template. The protocol can include a nucleotide delivery step whereby all four nucleotides are present in the sequencing reaction simultaneously, a detection step whereby the identity of each nucleotide species is distinguished according to the rate or time duration for a respective conformational signal change in the polymerase, a deblocking step to remove the reversible terminator moieties, and repetition of the aforementioned steps. Wash steps can be carried out to remove reaction components between one or more of the steps. Generally a single nucleotide will be identified for each repetition. After several repetitions, a single nucleic acid sequence that resolves the positions of all four nucleotide species can be obtained using the fourth exemplary protocol.

A fifth exemplary nucleic acid sequencing protocol can be carried out for a sequencing reaction that includes, inter alia, a primed nucleic acid template, conformationally labeled polymerase and a single nucleotide species, wherein the nucleotide species has a reversible terminator moiety. The protocol can include separate nucleotide delivery steps whereby each of four nucleotides are present in the sequencing reaction individually, a detection step whereby incorporation of the nucleotide species is determined according to the rate or time duration for a conformational signal change in the polymerase, a deblocking step to remove the reversible terminator moieties, and repetition of the aforementioned steps with the other three nucleotides. Wash steps can be carried out to remove reaction components between one or more of the steps. The four different nucleotide species differ in their base composition but not necessarily in the rate or time duration for a conformational signal change that occurs for the polymerase when each species is incorporated into the primed nucleic acid template. The four phase nucleotide delivery and detection protocol can be repeated for several cycles. Generally, a single nucleotide will be identified for each cycle of four phases. After several repetitions, a single nucleic acid sequence that resolves the positions of all four nucleotide species can be obtained using the fifth exemplary protocol.

A sixth exemplary nucleic acid sequencing protocol can be carried out for a sequencing reaction that includes, inter alia, a primed nucleic acid template, conformationally labeled polymerase and a set of four different nucleotide species, wherein each nucleotide species has a reversible terminator moiety. A first nucleotide of the set differs from the other three nucleotides in the rate or time duration for a conformational signal change that occurs for the polymerase when it is incorporated into the primed nucleic acid template. The other three nucleotides are not necessarily distinguished from each other based on the rate or time duration for a conformational signal change that occurs for the polymerase when they are incorporated into the primed nucleic acid template. The protocol can include a nucleotide delivery step whereby all four nucleotides are present in the sequencing reaction simultaneously; a detection step, whereby the identity of the first nucleotide species is distinguished from the other three nucleotide species according to the rate or time duration for a respective conformational signal change in the polymerase and whereby incorporation of the other three nucleotides is detected based on the conformational signal change; a deblocking step to remove the reversible terminator moieties; and repetition of the aforementioned steps. Wash steps can be carried out to remove reaction components between one or more of the steps. After several repetitions, a single nucleic acid sequence that resolves the positions of a single nucleotide species can be obtained using the second exemplary protocol.

A seventh exemplary nucleic acid sequencing protocol can be carried out as set forth above for the sixth exemplary nucleic acid sequencing protocol with the exception that a second set of nucleotides is used in place of the first set of nucleotides that was used in the sixth exemplary protocol. The second set of nucleotides can differ from the first set of nucleotides in the identity of the nucleotide that differs from the other three nucleotides in the rate or time duration for the conformational signal change. For example, the second set of nucleotides can include rtATP, rtdTTP, rtdCTP and γANSrtGTP ("rt" refers to the presence of a reversible terminator) whereas the first set of nucleotides included rtATP, rtTTP, γANSrtCTP and rtGTP. Again a single nucleic acid sequence that resolves the positions of a single nucleotide species (i.e. cytosine) can be obtained using the seventh exemplary protocol. Comparison of the results of the sixth and seventh sequencing protocol can provide a low resolution sequence of the nucleic acid template in which the position of two nucleotides (i.e. guanine and cytosine) is resolved.

An eighth exemplary nucleic acid sequencing protocol can be carried out for a sequencing reaction that includes, inter alia, a primed nucleic acid template, conformationally labeled polymerase and a single nucleotide species, wherein the nucleotide species is selected from naturally occurring nucleotides including dATP, dCTP, dGTP, dTTP, and dUTP. The protocol can include separate nucleotide delivery steps whereby each of four nucleotides are present in the sequencing reaction individually, a detection step whereby incorporation of the nucleotide species is determined according to the rate or time duration for a conformational signal change in the polymerase. Wash steps can be carried out to remove reaction components between one or more of the steps. The four phase nucleotide delivery and detection protocol can be repeated for several cycles. Generally, a single nucleotide will be identified for each cycle of four phases. After several repetitions, a single nucleic acid sequence that resolves the positions of all four nucleotide species can be obtained using the fifth exemplary protocol. When this exemplary protocol is carried out in a single molecule detection mode, the numbers of the homopolymers in the nucleic acid can be determined by counting the number of times the conformational change has happened as demonstrated by probes.

As set forth previously, a low resolution sequence can provide a useful scaffold for sequence alignment as set forth in U.S. Patent Publ. Nos. 2010/0173303 and 2010/0279882, each of which is incorporated herein by reference. Alternatively, the seventh exemplary nucleic acid sequencing protocol can be repeated using a third and fourth set of nucleotides whereby two different nucleotides are respectively distinguishable. Comparing the results of all four sequencing protocols can provide a single nucleic acid sequence that resolves the positions of all four nucleotide species in the nucleic acid template.

A ninth exemplary nucleic acid sequencing protocol can be carried out for a sequencing reaction that includes, inter alia, a primed nucleic acid template, conformationally labeled polymerase and a first set of two different nucleotide species. The two different nucleotide species in the first set differ in their base composition and in the rate or time duration for a conformational signal change that occurs for the polymerase when each species is incorporated into the primed nucleic acid template (e.g. γANSdGTP and dATP). The two different nucleotide species in the first set are extendable, for example, lacking terminator groups at the 3' position of the ribose moiety. The protocol can include delivery of the first set to the sequencing reaction such that the two nucleotides are present simultaneously and the conformational signal changes occurring in the polymerase are detected in real time, whereby the identity of each nucleotide species is distinguished according to the rate or time duration for the respective conformational signal change. An optional wash step can be carried out to remove unreacted nucleotides from the primed nucleic acid template. Then a second set of two different nucleotide species can be contacted with the primed nucleic acid template and a conformationally labeled polymerase, wherein the two nucleotides of the second set are present simultaneously and the conformational signal changes occurring in the polymerase are detected in real time and the identity of each nucleotide species in the second set is distinguished according to the rate or time duration for the respective conformational signal change. The second set of nucleotide species includes two different nucleotide species that differ from each other in their base composition and also differ in the rate or time duration for a conformational signal change that occurs for the polymerase when each species is incorporated into the primed nucleic acid template (e.g. γANSdCTP and dTTP). The nucleotides in the second set differ in base composition from the two nucleotides that were in the first set of nucleotide species; however, the nucleotides in the first set need not be distinguishable from the nucleotides of the second set with respect to the rate or time duration for a conformational signal change that occurs for the polymerase since the two set of nucleotides are delivered and detected in separate steps. Although the pairs of nucleotide species are delivered in separate steps, a single nucleic acid sequence that resolves the positions of all four nucleotide species can be obtained using the ninth exemplary protocol.

As exemplified by the protocols above, a polymerase extension method can be carried out by a single delivery of nucleotides or by multiple deliveries of nucleotides. In an exemplary embodiment, the former configuration can include a single delivery of several different species of nucleotides such that the polymerase is able to add several nucleotides to a growing nucleic acid strand. In such a method multiple nucleotide deliveries are not necessary to achieve extension of a primer by at least 2, 3, 5, 10, 50, 100, 250, 500, 1000, 10000 or more nucleotides. However, if desired multiple nucleotide deliveries can be performed and each delivery can include several different species of nucleotides such that the polymerase is able to add several nucleotides to a growing nucleic acid strand. Typically, four different nucleotide species will be delivered, but if desired, fewer than four can be delivered.

In a particular embodiment, one or more blocked nucleotide species can be added such that single base extension occurs. One or more blocked nucleotide species can be used in an embodiment whereby a polymerase extension method is carried out by a single delivery of nucleotides or by multiple deliveries of nucleotides. In an exemplary embodiment of the multiple nucleotide delivery format, several different species of reversibly blocked nucleotides can be present simultaneously in a reaction cycle. Deblocking and washing steps can be carried out between nucleotide addition steps. Thus, the sequencing procedure can be carried out as a series of repeated cycles of nucleotide delivery, detection and deblocking. The nucleotides can be delivered simultaneously or sequentially during each cycle. Washes can be carried out between steps of each cycle as desired to remove unwanted reactants or products from being present in subsequent cycles or subsequent steps of a current cycle.

Typically, nucleotides having different bases can be distinguished in a method set forth herein according to different moieties present on the respective nucleotide species. For example a dCTP can have a gamma phosphoamidate-linked moiety that is not present on a dGTP, thereby allowing incorporation of the dCTP into a nucleic acid to be distinguished from incorporation of the dGTP using a conformationally labeled polymerase. However if desired, a first and second population of nucleotides having a common base can have different moieties such that the two populations can be distinguished from each other in a method set forth herein. This is demonstrated by Example V, where incorporation of gamma-ANS-dTTP by a conformationally labeled polymerase is to be distinguished from incorporation of dTTP by the same polymerase.

Similarly, detection of time domain differences between different nucleotides when they are being incorporated or cleaved by a polymerase can be used for the detection of any of a variety of modifications of nucleic acids. For example, a methylated nucleotide can have a time domain signature that is unique from all other unmethylated nucleotides. Methods similar those set forth above and in the Examples below can be used to distinguish methylated from unmethylated nucleotides in a nucleic acid molecule.

Particular embodiments provide a method of determining nucleotide sequences which can optionally include the steps of (a) providing an array of different nucleic acid templates; (b) providing a mixture of nucleotide species, the mixture including (i) at least four different nucleotide species, (ii) at least one of the four different nucleotide species having a reversible terminator moiety, and (iii) at least two of the four different nucleotide species having an extendible 3' hydroxyl moiety; (c) contacting the array of nucleic acid templates with conformationally labeled polymerases and the mixture of nucleotide species under conditions wherein the conformationally labeled polymerases catalyze sequential addition of the nucleotide species to form nucleic acid complements of the nucleic acid templates, wherein the sequential addition of each different nucleotide species produces a conformational signal change from the conformationally labeled polymerase, wherein the rate or time duration for the conformational signal change is distinguishable for the at least two nucleotide species having the extendible 3' hydroxyl moiety, and wherein a plurality of the nucleic acid complements incorporate the at least one nucleotide species that has the reversible terminator moiety; (d) removing the reversible terminator moiety; (e) detecting a series of changes in the signal from the conformationally labeled polymerase at individual locations of the array; and (f) determining the sequence of nucleotides for the nucleic acid sample from the series of changes in the signal from the conformationally labeled polymerase.

As exemplified for the above embodiment, at least one nucleotide species having a reversible terminator moiety can be used in combination with nucleotide species that have an extendible 3' hydroxyl moiety. For example, different nucleotide species, each having a different base moiety capable of complementing one of four respective base species in a template nucleic acid, can be used. In this example at least one of the four different nucleotide species can have a reversible terminator moiety while the three other species have an extendible 3' hydroxyl group. Incorporation of the three extendible species into a nucleic acid can be distinguished as set forth herein, for example, based on differences in rate or time duration for signal changes that occur in a conformationally labeled polymerase that incorporates the nucleotides into the nucleic acid. The incorporation of the nucleotide species having the reversible terminator can be distinguished from the other three nucleotide species based on the termination in extension that occurs for the nucleic acid. For embodiments that use a conformationally labeled polymerase, the termination can be detected as a pause in the detection of conformational changes in the polymerase. The termination can be reversed using a deblocking reagent as set forth previously herein and, if desired, extension can then be resumed. Thus, the termination that resulted from incorporation of the nucleotide species having the reversible terminator can be distinguished from the other three nucleotide species based on the resumption of extension after treatment of the nucleic acid with the deblocking reagent.

For ease of description the example above describes use of a single nucleotide species having a reversible terminator moiety in combination with 3 other nucleotide species having an extendible 3' hydroxyl moiety. It will be understood that more than one reversibly blocked nucleotide species can be used with extendible nucleotide species in a method set forth herein. For example, different nucleotide species, each having a different base moiety capable of complementing one of four respective base species in a template nucleic acid, can include at least one, two, three, or four species having a reversible terminator moiety. In particular embodiments, a mixture of four different nucleotide species can include no more than 1 species having a reversible terminator moiety and at least 3 different species having an extendible 3' hydroxyl; no more than 2 different species having a reversible terminator moiety and at least 2 different species having an extendible 3' hydroxyl; or no more than 3 different species having a reversible terminator moiety and at least 1 species having an extendible 3' hydroxyl. Of course, some embodiments can include 4 different species having a reversible terminator moiety. The combinations of nucleotide species exemplified above can be provided in a mixture that is contacted with a nucleic acid sample or the nucleotides can be provided to a nucleic acid sample individually, for example, in a stepwise manner.

Methods that employ a nucleotide species having a reversible terminator moiety are typically carried out in repeated cycles. In embodiments that utilize a combination of nucleotides having reversible terminator moieties and extendible 3' hydroxyl groups, it is possible to extend at least some nucleic acid sequences with several nucleotide additions. Extension will continue due to the incorporation of extendible nucleotides up until a reversibly terminated nucleotide is incorporated. The incorporation of each nucleotide species can be detected, and in many embodiments the species of nucleotide that is incorporated can be distinguished, as set forth elsewhere herein. A deblocking step can be used to remove reversible blocking moieties from an extended nucleic acid. For example, a deblocking reagent can be used to remove a chemically labile blocking moiety or light can be used to remove a photolabile blocking moiety. Extension and detection steps can then be carried out again. Several repetitions of the extension, detection and deblocking steps can be carried out for a nucleic acid, for example, to determine the sequence of nucleotides for the nucleic acid.

In particular embodiments, at least one species of nucleotide that is used in a method set forth herein can be present at a concentration that is substantially lower than the concentration of another nucleotide species used in the method. As a result, the nucleotide species that is present at low concentration can produce a signal change in a conformationally labeled polymerase that is distinguishable from the change occurring for other nucleotide species that are present at higher concentration. The distinction can be made, for example, based on altered rate or time duration for a signal change. The concentration of one or more nucleotide species used in a method can be selected to result in a low branching ratio. Branching is the binding of the appropriate nucleotide to a polymerase without productive incorporation of the nucleotide into a nucleic acid molecule by the polymerase.

Particular embodiments of methods of determining nucleotide sequences can use a mixture of nucleotide species, wherein the mixture includes (i) at least four different nucleotide species, (ii) at least one of the four different nucleotide species having a reversible terminator moiety, (iii) at least two of the four different nucleotide species having an extendible 3' hydroxyl moiety, and (iv) at least one of the four different nucleotide species being present at a substantially lower concentration than the concentration of any other nucleotide species in the mixture. Specifically, the nucleotide that is present at the substantially lower concentration can be present at a concentration that produces a distinguishable rate or time duration for the conformational signal change.

The following examples are intended to illustrate but not limit the present invention.

Example I

Polymerase Engineering

A panel of polymerases from family A and family B including Klenow fragment, T7 polymerase, Bst polymerase, 9° N polymerases, KOD, RB69 polymerase, Phi29 polymerase and/or Bsu polymerase, is surveyed. Native Cys residues are replaced by Ser, Val, or Ala using known site-directed mutagenesis techniques. Molecular modeling based on existing crystal structures such as those described in Berman et al. *EMBO J.* 26: 3494-3505 (2007), and Kamtekar et al. *EMBO J.* 25: 1335-1343 (2006), each of which is incorporated herein by reference, are used to identify pairs of locations where the relative movements caused by the conformational changes of the polymerases between the open and the closed conformations are maximum and easily detectable by probes. Candidates are shown in FIG. 2. The amino acid residues at the chosen pairs of locations are changed to Cys residues by site-directed mutagenesis.

The resulting double Cys mutants are then expressed in *E coli* and purified using affinity chromatography via a genetically fused His-tag, GST-tag, and/or Heparin affinity column.

Labeling of the double Cys mutants with sulfhydryl specific probes, such as fluorophores, follows manufacturers' recommendations and/or techniques described in Santoso et al. *Proc. Nat'l. Acad. Sci. USA* 107:705-710 (2010), incorporated herein by reference. In short, the double-Cys mutant proteins are labeled by sequential addition of two maleimide fluorophores. The two fluorophores compose a FRET pair. The first maleimide fluorophore is added to protein at 1:1 molar ratio and incubated at 22° C. at 2 hours. Labeling occurs predominantly at the Cys residue that is more surface exposed and has higher reactivity. The second maleimide fluorophore is then added at high molar excess for an additional 10 hours. The reaction is stopped by addition of dithiothreitol to 1 mM, and the unincorporated fluorophores are removed by gel filtration on a Bio-Spin 30 column.

The activity of the doubly-labeled polymerases is assessed by measuring the rate of nucleotide addition to a DNA primer terminus by chemical quench methods as described in Joyce et al. *Biochemistry* 47:6103-6116 (2008), and Johnson K A. *Methods Enzymol* 249:38-61 (1995), each of which is incorporated herein by reference.

Optionally, the active doubly labeled polymerase is then used as the backbone for further mutagenesis, to generate polymerase variants that can incorporate and extend unnatural nucleotides at a desirable rate.

Molecular modeling based on crystal structures is exploited to identify the locations of the polymerases where mutations can be made to allow faster or slower incorporation and extension of unnatural nucleotides. Residue(s) identified as targets for replacement are replaced with a residue or residues selected using energy minimization modeling, homology modeling, and/or conservative amino acid substitutions to determine best case selections derived from known best substitution tables. Such strategies are well known in the art as described, for example, in Bordo, et al. *J Mol Biol* 217: 721-729 (1991), which is incorporated herein by reference. These strategies can be used to generate a library of mutants with desired substitutions, which can then be assayed for incorporation and extension rates relative to a parental polymerase, as described below. Generation of libraries is well described in the art such as Hayes, et al. *Proc Natl Acad Sci, USA* 99: 15926-15931 (2002), which is incorporated herein by reference.

Example II

Creation of Nucleotide Sets for Sequencing

Stopped-flow fluorescence kinetic analysis is used in accordance with techniques known in the art such as those described in Johnson, et al. *The Enzymes XX,* 1-61 (1992), which is incorporated herein by reference. Measurements are performed on polymerases such as those engineered as set forth above in Example I to obtain the rates of both incorporation and extension of natural and unnatural nucleotides.

A panel of unnatural nucleotides, including for example those set forth herein above, is tested for one or more polymerases until four distinctive rates are obtained for the four nucleotides corresponding to dATP, dCTP, dGTP, and dTTP. The selected polymerase mutant and four unnatural nucleotides are used for single molecule detection and sequencing methods.

Example III

Detection of Nucleotide Incorporation into a Nucleic Acid Using FRET-Labeled Polymerase The Klenow Fragments (KF) was produced as follows. KF was mutated to replace cysteine 907 with glycine, to replace leucine 744 (in the fingers domain) with cysteine and to replace lysine 550 (in the thumb domain) with cysteine, thereby producing K550C/L744C/C907G KF. Standard mutagenesis techniques were used to produce K550C/L744C/C907G KF as described in the manual of the QuikChange® site-directed mutagenesis kit from Stratagene/Agilent (La Jolla, Calif.). The K550C/L744C/C907G KF was cloned into the pET15b plasmid using the NdeI and BamHI restriction sites, and expressed in *E. coli* BL21(DE3) cells. The K550C/L744C/C907C KF was purified as described in Joyce, et al. *Biochemistry*, 47 (23): 6103-6116 (2008), which is incorporated herein by reference. The purified K550C/L744C/C907C KF was chemically modified using the thiol-reactive maleimide to introduce the Alexa488 fluorescent donor dye at cysteine 550

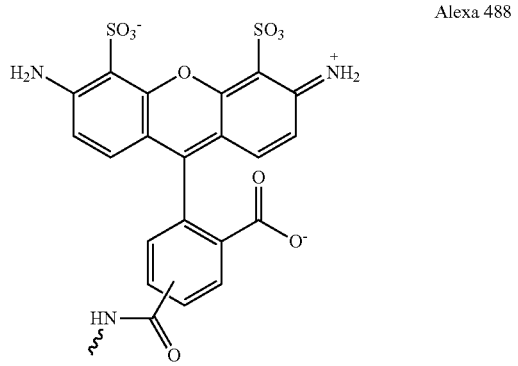

Alexa 488 and to introduce the Alexa532 fluorescence acceptor dye at cysteine 744,

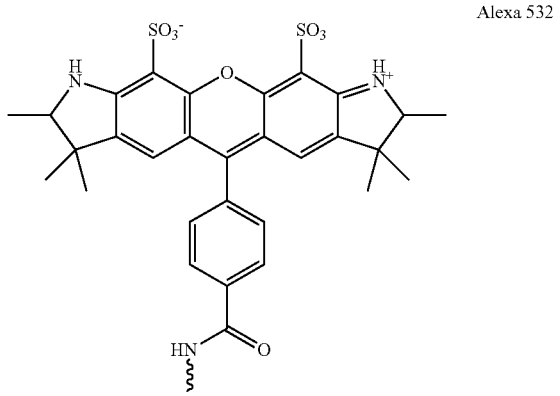

Alexa 532 thereby producing Alexa 488 and 532 dual-labeled KF. The thiol-reactive dye labeling protocol is described in *Molecular Probes: The Handbook* (Invitrogen, Carlsbad Calif.), which is incorporated herein by reference.

Conformational changes in the dual labeled KF enzyme from the open to closed state can be detected based on fluorescence resonance energy transfer (FRET) between the AF488 fluorescent donor dye on the thumb domain and AF532 fluorescence acceptor dye on the fingers domain. The KF enzyme can be bound to a primer-template nucleic acid complex in an open conformation. In the open conformation the AF488 fluorescent donor dye when excited with light at a wavelength of 495 nm will emit fluorescence at a wavelength of 519 nm. However, upon binding of an appropriate nucleotide to the dual labeled KF-template-primer complex the dual labeled KF enzyme changes from the open state to the closed state. The closed state brings the AF488 fluorescent donor dye on the thumb domain into proximity with the AF532 fluorescence acceptor dye on the finger domain such that the AF488 fluorescent donor dye when excited transfers energy to the AF532 fluorescence acceptor dye. This FRET results in a detectable emission from the AF532 fluorescence acceptor dye at a wavelength of 531 nm. As such, binding of the appropriate nucleotide can be detected as increased emission at 554 nm wavelength. Furthermore, differential time durations of the closed state can be used to distinguish different nucleotides that are incorporated into the primer by dual labeled KF.

The real-time fluorescence change from dual labeled KF was measured in an Applied Photophysics SX20 stopped-flow spectrometer by monitoring changes in AF 488 dye fluorescence following the mixing of the PolI(KF)-DNA binary complex with a nucleotide in the reaction buffer containing 10 mM Tris-HCl, pH 8.0, 50 mM NaCl, 1 mM dithiothreitol and 10 mM $MgCl_2$.

Figure 5:
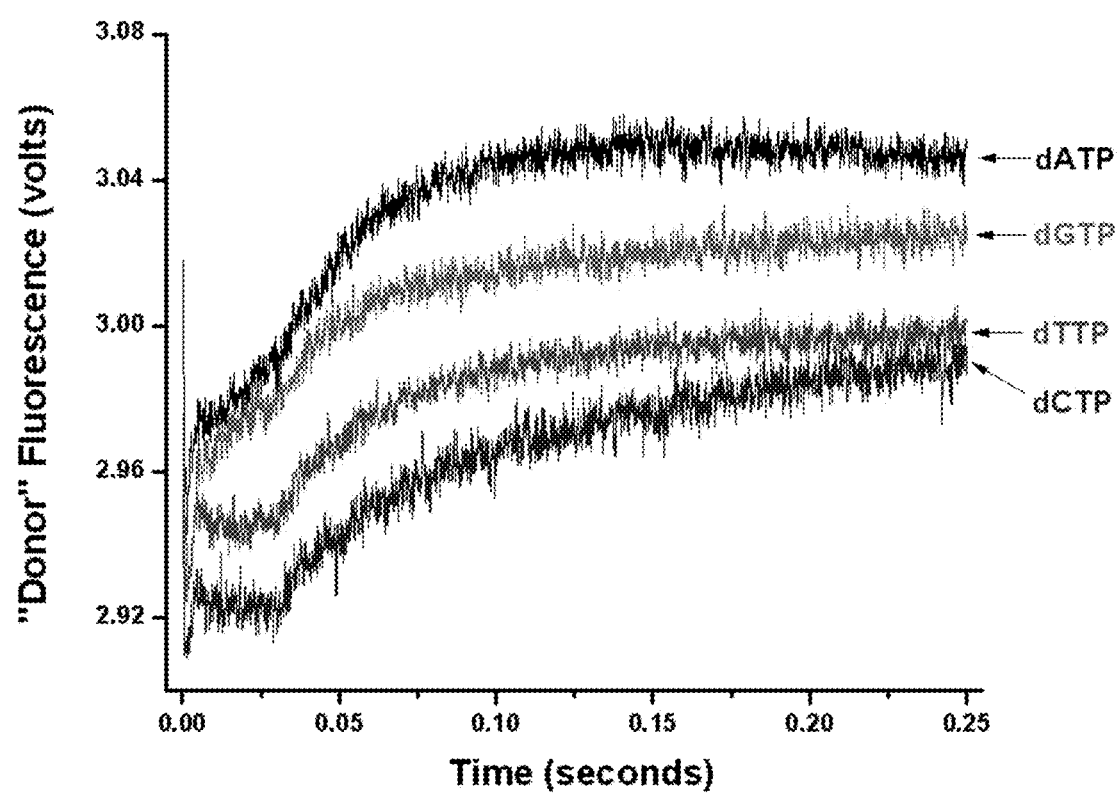
FIG. 5 shows a plot of donor fluorescence vs. time for incorporation of natural nucleotides dATP, dGTP, dTTP and dCTP into a template bound primer by a conformationally labeled polymerase.

As shown in FIG. 5 the incorporation of natural nucleotides into the primer could be detected based on FRET signals from dual labeled KF. However, the time durations of the FRET signal for the natural nucleotides dATP, dGTP, dTTP and dCTP were very similar.

Figure 6A:
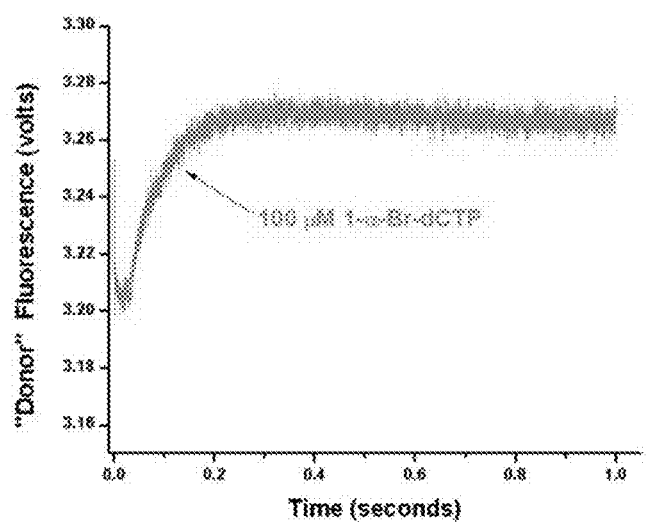
FIG. 6A-C shows a plot of donor fluorescence vs. time for incorporation of nucleotides 1-alpha-bromo-dCTP (panel A), 1-alpha-thiol-dCTP (panel B) and dCTP (panel C) into a template bound primer by a conformationally labeled polymerase.
Figure 6B:
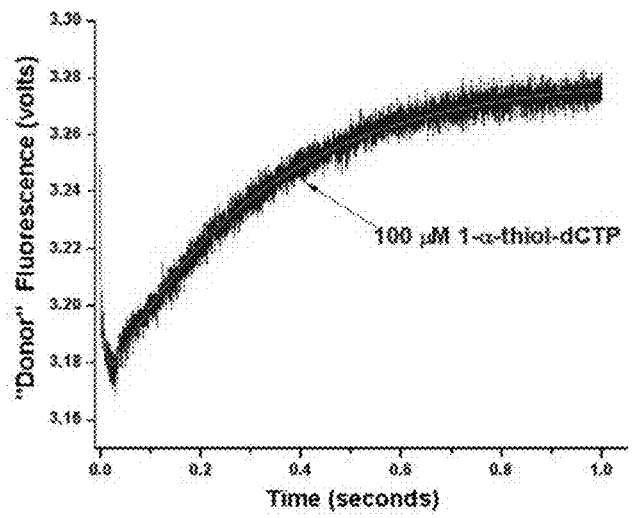
Figure 6C:
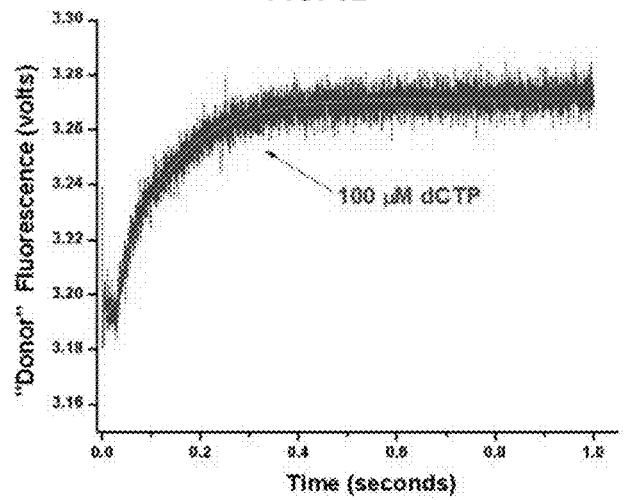
Figure 7:
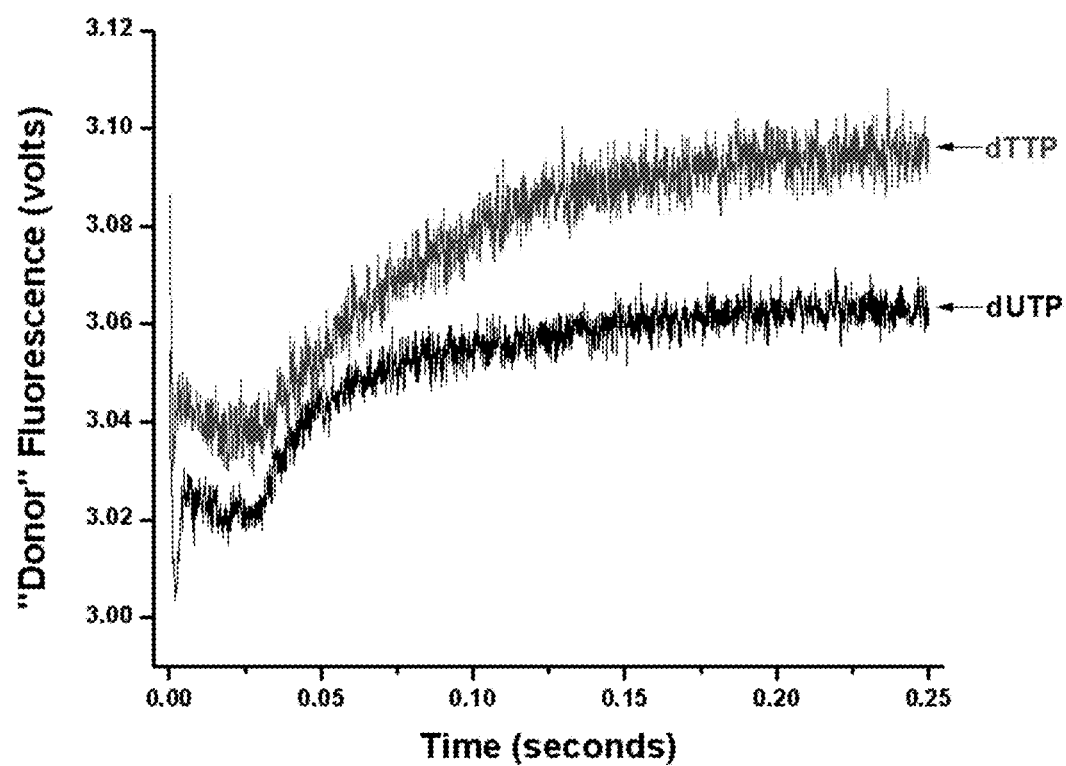
FIG. 7 shows a plot of donor fluorescence vs. time for incorporation of nucleotides dTTP and dUTP into a template bound primer by a conformationally labeled polymerase.

In contrast, FRET duration could be modulated by using non-natural nucleotides. As shown in FIG. 6, the FRET durations measured for the incorporation of dCTP, 1-alpha-thiol-dCTP and 1-alpha-borano-dCTP were substantially different. Similarly, the FRET durations measured for the incorporation of dTTP differed from those measured for incorporation of dUTP (see FIG. 7).

Figure 8:
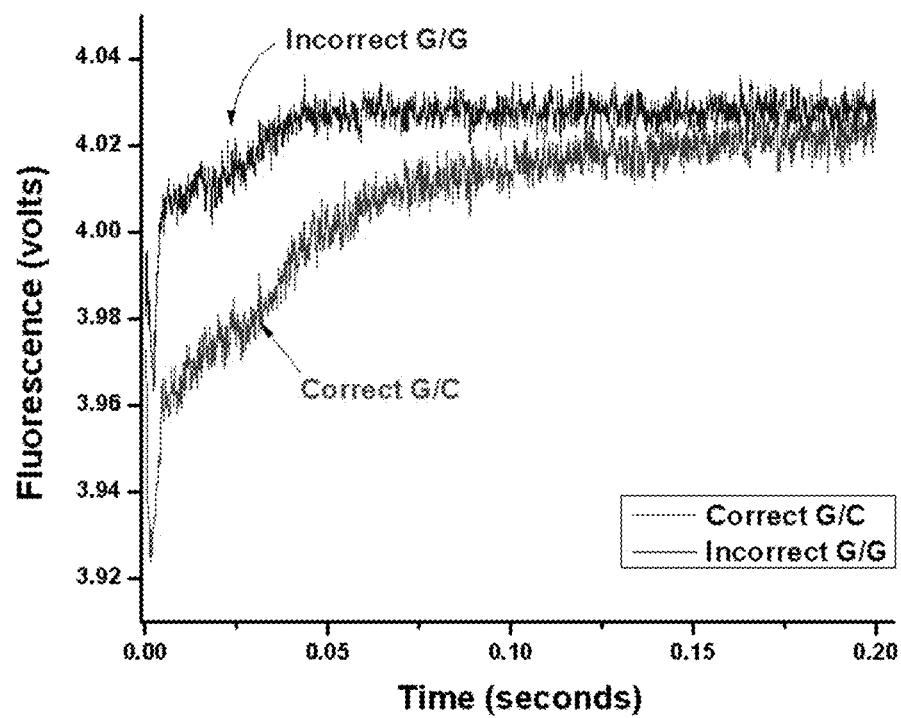
FIG. 8 shows a plot of donor fluorescence vs. time for incorporation of correct and incorrect nucleotides into a template bound primer by a conformationally labeled polymerase.

As shown in FIG. 8, the incorporation of a correct dGTP nucleotide at a position that was complementary to cytosine could be distinguished from the incorrect incorporation of dCTP at the same position based on differences in FRET duration.

This example demonstrates that the incorporation of a nucleotide into a growing primer nucleic acid can be detected using a conformationally labeled polymerase having a pair of FRET probes. This example further demonstrates that the incorporation of different nucleotides by a conformationally labeled polymerase can be distinguished based on differences in the time duration for a conformational signal change produced by the conformationally labeled polymerase. This example also demonstrates that the time duration for a conformational signal change produced by the conformationally labeled polymerase can be modulated by using non-natural nucleotide analogs.

Example IV

Detection of Nucleotide Incorporation into a Nucleic Acid by a Polymerase Having an Environment-Sensitive Dye 5-TAMRA Pol β was prepared as follows. Human Pol β was mutated to replace Tryptophan 325 (in the fingers domain)

with cysteine to produce W325C Pol β. Standard mutagenesis techniques were used to produce W325C Pol β as described in Example III. The W325C Pol β was cloned in the pET15b plasmid, expressed in *E. coli* BL21(DE3) cells and purified as described in Dunlap and Tsai, *Biochemistry*, 41 (37): 11226-11235 (2002), which is incorporated herein by reference. The purified W325C Pol β was chemically modified to introduce the 5-TAMRA fluorescent dye at cysteine 325, thereby producing 5-TAMRA Pol β.

Conformational changes in the 5-TAMRA Pol β enzyme from the open to closed state can be detected based on a fluorescent emission change from the environmentally sensitive 5-TAMRA dye. The spectral and emission intensity changes from the 5-TAMRA dye when the polymerase changes to the closed state. The 5-TAMRA Pol β enzyme can be bound to a primer-template nucleic acid complex in an open conformation. In the open conformation the 5-TAMRA dye when excited with light at a wavelength of 542 nm will emit fluorescence at a wavelength of 568 nm. However upon binding of an appropriate nucleotide to the 5-TAMRA Pol β—primer-template binary complex, the 5-TAMRA Pol β enzyme changes from the open state to the closed state causing the 5-TAMRA dye to experience a different environment. This change in environment results in a detectable fluorescent emission change from the TAMRA dye at the wavelength of 568 nm. As such, binding of the appropriate nucleotide can be detected as a fluorescent emission change at 568 nm wavelength. Furthermore, differential time durations of the closed state can be used to distinguish different nucleotides that are incorporated into the primer by 5-TAMRA Pol β.

The real-time fluorescence change from 5-TAMRA Pol β was measured in the Applied Photophysics SX20 stopped-flow spectrometer by monitoring changes in 5-TAMRA dye fluorescence following the mixing of the 5-TAMRA Pol β-DNA binary complex with a nucleotide in a reaction buffer containing 50 mM Tris-HCl, pH 7.5, 50 mM KCl, 1 mM Dithiothreitol and 5 mM MgCl$_2$ as described in Example III.

Figure 9A:
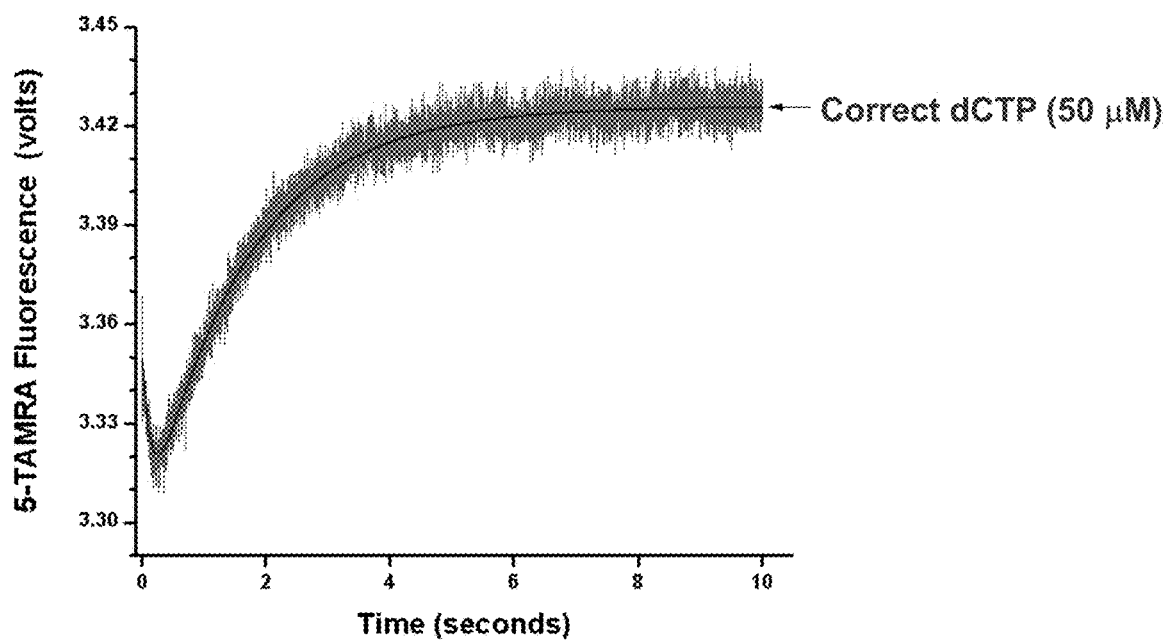
FIG. 9A-B shows a plot of 5-TAMRA fluorescence vs. time for incorporation of correct nucleotide (panel A) and incorrect nucleotides (panel B) into a template bound primer by a conformationally labeled polymerase.
Figure 9B:
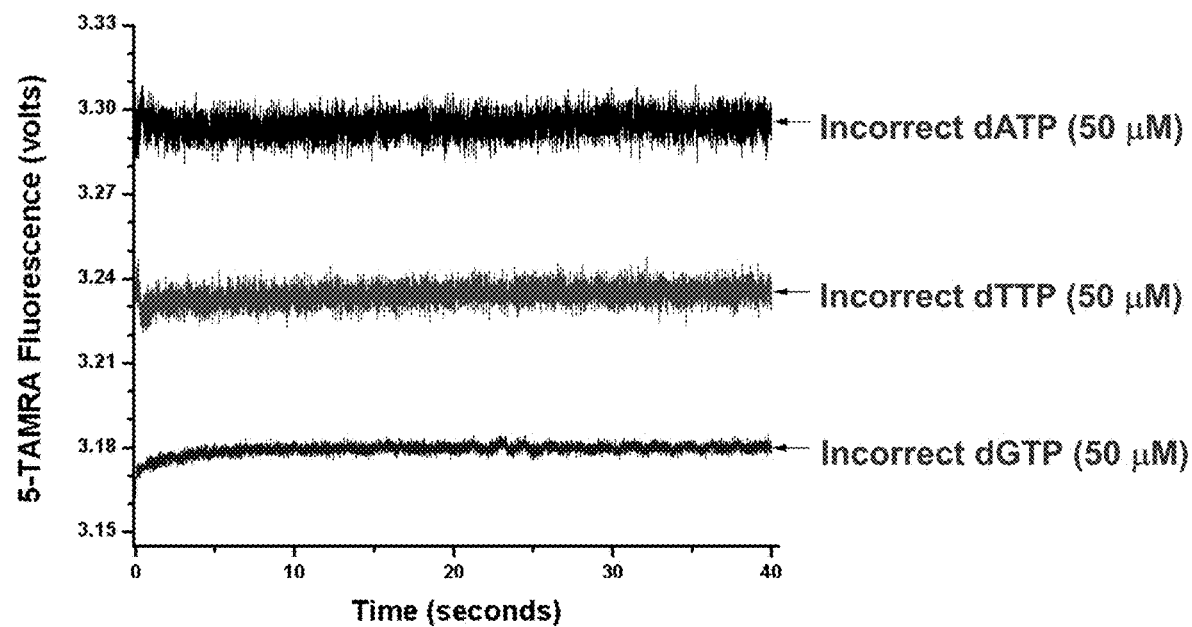

As shown in FIG. 9A, incorporation of a correct dCTP nucleotide into the 5-TAMRA Pol β could be detected based on the wavelength shift for the 5-TAMRA dye. Furthermore, as shown in FIG. 9B, incubation of the polymerase with incorrect nucleotides did not yield a substantial shift in 5-TAMRA emission.

Different nucleotides, dATP, dTTP, dCTP and dGTP produced different amplitudes and durations for the 5-TAMRA emission shift when incorporated at an appropriate position in a template-bound primer (see FIG. 10). Furthermore, non-native nucleotide analogs 1-alpha-thiol-dCTP and 1-alpha-borano-dCTP could be distinguished from each other as well (see FIG. 11). As such the different nucleotide species could be distinguished using 5-TAMRA Pol β as a reporter.

This example demonstrate that the incorporation of a nucleotide into a growing primer nucleic acid can be detected using a conformationally labeled polymerase having an environmentally sensitive dye. This example further demonstrates that the incorporation of different nucleotides by the conformationally labeled polymerase can be distinguished based on differences in the time duration for a conformational signal change produced by the conformationally labeled polymerase. This example also demonstrates that the time duration for a conformational signal change produced by the conformational labeled polymerase can be modulated by using non-natural nucleotide analogs.

Example V

Detection of Gamma-Phosphate Modified Nucleotide Incorporation into a Nucleic Acid Using Conformationally-Labeled Polymerase Dual labeled KF was produced as described in Example III. FRET from dual labeled KF was measured by stopped flow kinetics also as described in Example III. 5-TAMRA Pol β was prepared as described in Example IV. The real time fluorescence change from 5-TAMRA Pol β was measured by stopped flow kinetics also as described in Example IV.

Gamma-ANS-dTTP was synthesized as described in Mulder et al., *Nucleic Acids Res.* 33:4865-4873 (2005) and Berde et al., *J. Biol. Chem.* 254:12069-12073 (1979), each of which is incorporated herein by reference.

Figure 13A:
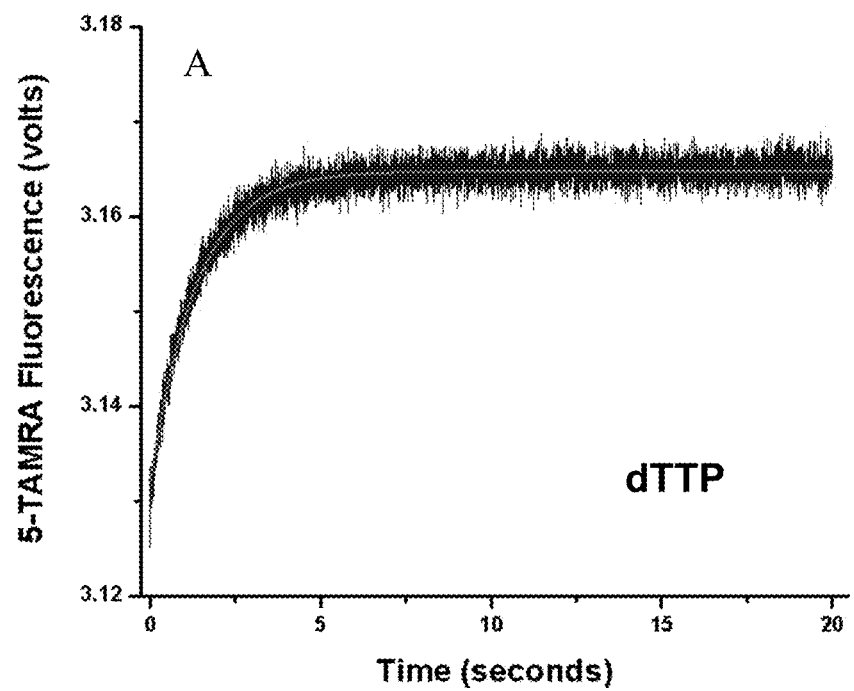
FIG. 13A-B shows a plot of 5-TAMRA fluorescence vs. time for incorporation of dTTP (Panel A) and γ-dTTP (Panel B) into a template bound primer by a conformationally labeled polymerase.
Figure 13B:
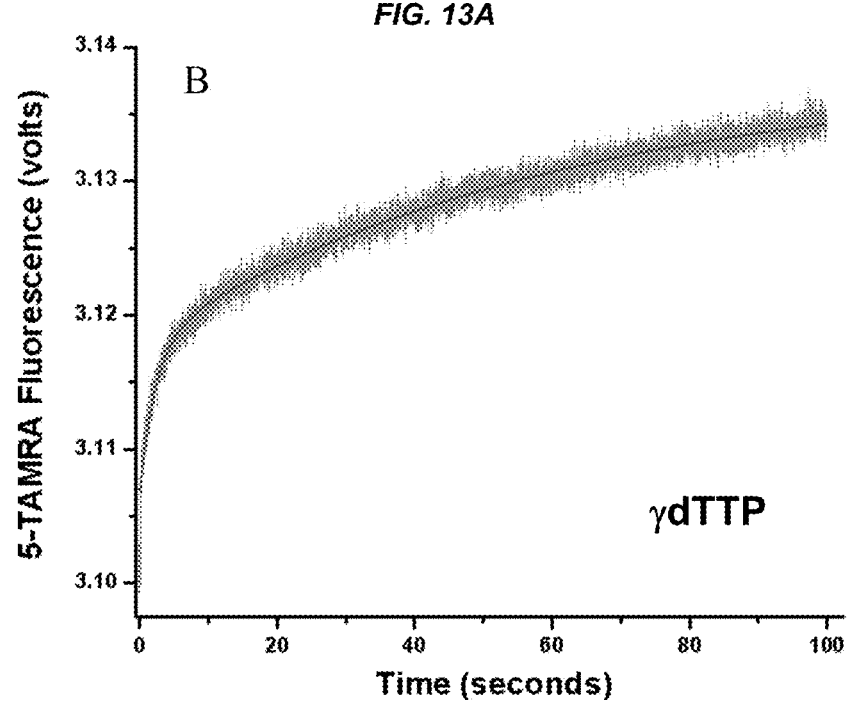

As shown in FIG. 12 the AF488 fluorescence duration measured for the incorporation of dTTP and Gamma-ANS-dTTP by dual labeled KF were substantially different. Similarly, incorporation of dTTP and Gamma-ANS-dTTP by 5-TAMRA Pol β could be distinguished from each other (see FIG. 13).

This example demonstrates that the incorporation of a gamma-phosphate modified nucleotide by a conformationally labeled polymerase can be distinguished from incorporation of a natural nucleotide based on differences in the time duration for a conformational signal change produced by the conformationally labeled polymerase.

Example VI

Light-Gated Sequencing

FIG. 14A shows a diagrammatic representation of a light-gated sequencing reaction. A sample is provided having conformationally labeled DNA polymerase, primer-template DNA complexes, a first nucleotide species (caged) and a second nucleotide species.

Individual primer-template DNA complexes are separated from each other on an array surface to allow conformational signal changes for polymerases bound to each complex to be detected at a single-molecule level.

Caged nucleotide species 1 has a photo-cleavable NPE moiety attached to the 5' gamma phosphate. The NPE moiety prevents caged nucleotide species 1 from binding to the conformationally labeled polymerase. The NPE moiety is photo-cleavable by irradiation with UV light to produce uncaged nucleotide species 1. Uncaged nucleotide species 1 is able to bind the conformationally labeled polymerase and can be incorporated into the primer strand of the primer-template complex. Nucleotide species 2 has a gamma-ANS moiety. The time duration for the conformational signal change of the conformationally labeled polymerase is longer for nucleotide species 2 than for uncaged nucleotide species 1.

A low power light pulse is delivered to the sample such that a subpopulation of caged nucleotide species 1 becomes uncaged (by photo-cleavage of the NPE moiety). The light pulse initiates the polymerase extension reaction because the base moiety of the uncaged nucleotide species complements the first position of the template strand. The time duration for conformational signal changes at each array feature (i.e. an individual polymerase bound to an individual primer-template complex) is detected. A sequence of time durations, measured for an individual array feature, is shown in FIG. 14B. As shown in the figure, incorporation of the two species can be distinguished based on different time durations for the signal changes they cause in the polymerase. Specifically, the sequence of incorporations following the first uncaging light pulse is 1111122211 (where "1" represents uncaged nucleotide species 1 and "2" represents nucleotide species 2).

As shown in FIG. 14A, the extension reaction will terminate when the subpopulation of uncaged nucleotide species 1 has been substantially depleted and the polymerase arrives at a location in the template that complements species 1. The extension reaction can be resumed by delivering a second low power light pulse to the sample such that a second population of caged nucleotide species 1 become uncaged.

For clarity of description the example of FIG. 14B shows the extension reaction going until depletion of uncaged nucleotide followed by delivery of the second light pulse. It is however, desirable in some embodiments to deliver light pulses prior to depletion of reagents. For example, light pulses can be delivered on a preset schedule. The rate of delivery for light pulses can also be controlled in response to a feedback loop that determines the extension rate for one or more polymerases in a sample. A rate of extension that is below a threshold rate would be indicative of reduced nucleotide concentration, in which case the duration or intensity of light pulses can be increased to bring the extension rate above the threshold. Conversely, a rate of extension that is above a ceiling rate would be indicative of excess nucleotide concentration, in which case the duration or intensity of light pulses can be decreased to bring the extension rate below the ceiling.

For purposes of illustration this example has been described with respect to a system having two nucleotide species, one of which is caged. Similar systems can use 3, 4 or more nucleotides and of those nucleotides 1, 2, 3, 4 or more of the species can be caged. Furthermore, the different nucleotide species can be uncaged using different wavelengths of light.

Example VII

Design, Creation, Production and Analysis of a Conformationally Labeled Polymerase Family B RB69 DNA polymerase was modified to create the RB69V410CE766C conjugate. The structure of RB69 has been solved at 2.8 Å resolution in the open and closed states as described in Wang et al., Cell 89:1087-1099 (1997), which is incorporated herein by reference. Here the structures were analyzed revealing that the O-helix in the finger domain undergoes a 60° rotation upon nucleotide binding, which corresponds to a change of about 27 Å in the α-α carbon distance between the amino acids at positions 410 and 766. In the open position the amino acids are 69.4 Å apart and in the closed position they move to within 41.5 Å of each other. Förster Resonance Energy Transfer (FRET) is a method which can be used to detect a polymerase conformational change. The Förster radius (Ro) is the radius at which energy transfer between a donor dye and an acceptor dye is equal to 0.5. Energy transfer scales as approximately $1/r^6$ (where r=distance between a donor and acceptor dye) which makes it advantageous to position dyes at the Ro. The Ro for most standard commercial dyes is in the 50-70 Å range.

Cysteine residues are generally reactive toward a wide range of commercially available dyes. Therefore, RB69 was mutated as follows. Native Cysteine (C) residues were mutated to other natural amino acids at the following positions C41A, C57V, C456V, C609L, C671A, C748A, C801T, C845V. Also, native residues at positions 510 and 766 were substituted with C (V510C and E766C, respectively) to provide locations on the polymerase for site specific labeling. The resulting polymerase is referred to as RB69V510CE766C.

RB69V510CE766C was expressed in BL21(DE3) cells. Cells were grown in Terrific Broth (TB) at 37° until an OD of 0.8. The temperature was then reduced to 18 degrees and protein expression was induced with 0.5 mM IPTG. Cells were grown for an additional 16 hours. Following harvesting, the resulting cell pellet was lysed using a microfluidizer and the lysate treated with PEI to precipitate cellular DNA/RNA. PEI treatment was followed by ammonium sulfate (AS) fractionation. The (AS) pellet containing RB69V510CE766C was resolubilized and loaded onto a heparin column. RB69 was eluted from the heparin column using a salt gradient. The resulting peak fractions were pooled, concentrated, and loaded onto a Superdex 200 column for size exclusion chromatography. The resulting peak fractions were pooled, and purity confirmed by SDS-page gel.

Sulfhydryl reactive dyes were covalently attached to the cysteine residues of purified RB69V510CE766C as follows. Purified RB69V510CE766C was first treated with 10 mM dithiothreitol (DTT) for 30 min at room temperature to reduce disulfide bonds. Next, RB69V510CE766C was purified by fractionating with a Sephadex-25 column using the following buffer: 50 mM ACES pH 7.0, 1 M NaCl, 1 mM EDTA, and 0.01% w/v Tween-20. The fractions with RB69V510CE766C were identified by measuring the 280 nm absorption for each fraction. The RB69V510CE766C concentration was estimated using the 6280=150000 $M^{-1}cm^{-1}$ (Wang et al., Biochemistry 43:3853-3861 (2004), incorporated herein by reference). Then, conjugation reactions were carried out to label RB69V510CE766C with one of the following donor/acceptor pairs: Cy3/AF647 or CF555/AF647 (Cy3-maleimide was obtained from GE Healthcare, CF555-maleimide was obtained from Biotium and AF647-maleimide was obtained from Life Technologies). The dyes were in 100× molar excess relative to the RB69V510CE766C concentration and various donor/acceptor ratios were titrated to achieve nearly a 1:1:1 RB69V510CE766C:donor:acceptor ratio. The dye conjugation reaction proceeded for 12 h at 4° C. The RB69V510CE766C polymerase conjugate was purified using two steps. First, a Sephadex-25 column was used to separate the labeled conjugate from free dyes using 50 mM Tris pH 7.5, 1 M NaCl, 1 mM EDTA, 0.01% w/v Tween-20. The fractions containing the labeled conjugates were identified by measuring the absorption spectrum for each fraction. The fractions with product were pooled and dialyzed against 50 mM Tris pH 7.5, 1 M NaCl, 1 mM EDTA, 0.01% w/v Tween-20 for >4 h at 4° C. The absorption spectrum for final product was used to determine the degree of dyes per polymerase using the dye supplier's specifications.

Figure 15:
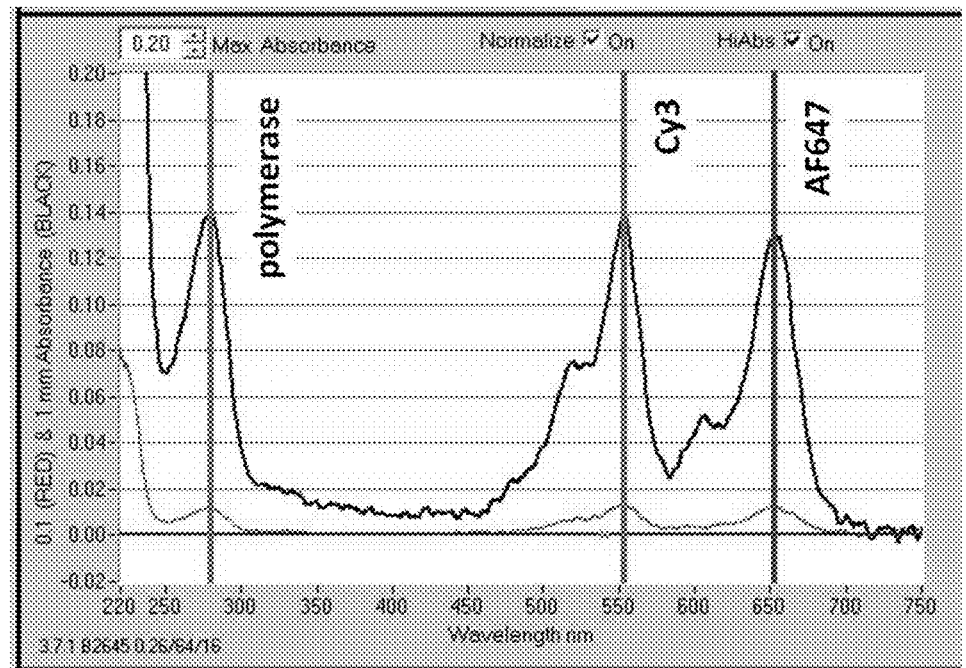
FIG. 15 shows an absorption spectrum for a conformationally labeled polymerase. The absorption peaks for the polymerase, Cy3 and AF647 are demarcated.

FIG. 15 shows an absorption spectrum for purified RB69V510CE766CCy3AF647 conjugate. The ratio of RB69V510CE766C:Cy3:AF647 was determined to be 1:1:0.7 from the spectrum.

Figure 16:
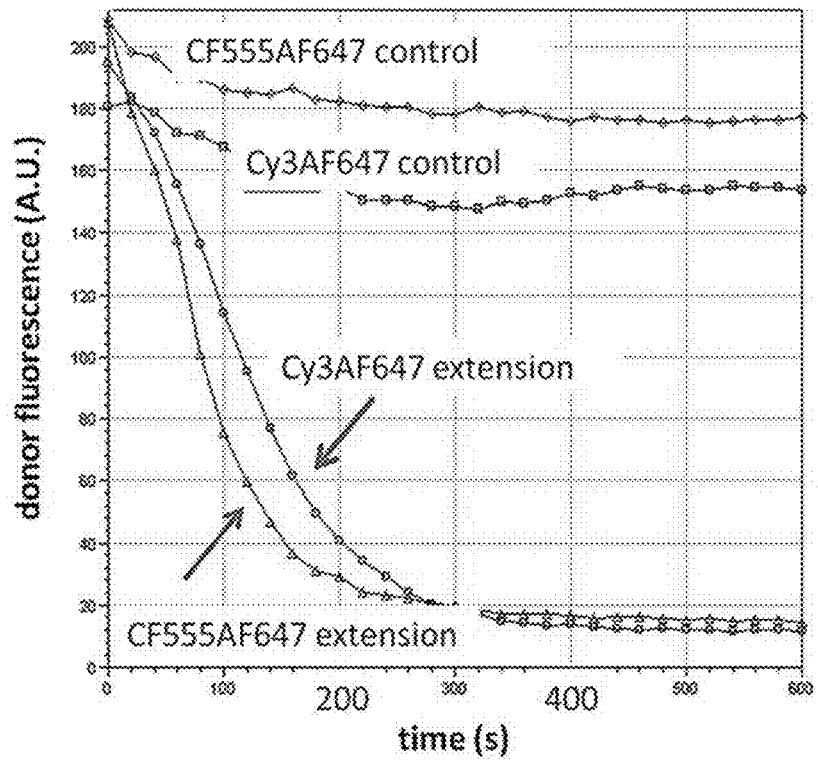
FIG. 16 shows a plot of fluorescence quenching vs. time for a polymerase extension reaction

Functionality of the Cy3AF647 and CF555AF647 conjugates of RB69V510CE766C were confirmed using a FRET-based primer extension assay as follows. Extension was carried out on a nucleic acid duplex composed of an extendable 3'-OH primer and a template with a 7 base overhang. The extendable sequence was TGGAACG. In addition, the template contained an AF488 dye at the 5' position. The extension reaction mix was composed of 50 mM ACES pH 7.2, 50 mM NaCl, 10 mM DTT, 10 mM $Mg^{2+}$, 1 µM dTTP, 1 µM dGTP, 1 µM dATP and 0.1 µM Cy3-dCTP. Upon extension, the Cy3 quenches the AF488. The control reactions were carried out under the same conditions except that dTTP was removed to prevent extension. A SpectraMax M5 plate reader was used to monitor the AF488 quenching over time. FIG. 16 shows a plot of AF488 fluorescence vs. time for the extension reaction. The plot confirms that both conjugates were functional in extending a primed nucleic acid.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of determining a sequence of nucleotides for a nucleic acid sample, comprising
    providing an array of nucleic acid templates, wherein the nucleic acid templates comprise nucleotide sequence fragments of the nucleic acid sample;
    contacting the array of nucleic acid templates with;
        (i) a conformationally labeled polymerase, wherein the conformationally labeled polymerase comprises a finger domain labeled with a first fluorescent label and a thumb domain labeled with a second label, wherein the first fluorescent label and second label are FRET pairs or wherein the second label is a quencher; and
        (ii) at least four different nucleotide species under conditions wherein the conformationally labeled polymerase catalyzes sequential addition of the nucleotide species to form nucleic acid complements of the nucleic acid templates, wherein the different nucleotide species comprise at least one non-natural nucleotide analog, wherein the sequential addition of each different nucleotide species produces a conformational fluorescent signal change from the conformationally labeled polymerase and wherein the rate or time duration for the conformational fluorescent signal change is distinguishable for each different nucleotide species;
    detecting a series of changes in the signal from the conformationally labeled polymerase under the conditions and at individual locations of the array; and
    determining the rates or time durations for the changes in the signal at the individual locations of the array, thereby determining the sequence of nucleotides for the nucleic acid sample.

2. The method of claim 1, wherein the providing the array comprises amplifying portions of the nucleic acid sample to produce the nucleotide sequence fragments.

3. The method of claim 1, wherein the providing the array comprises adding a universal sequence to the nucleotide sequence fragments to form tailed fragments and hybridizing the tailed fragments to oligonucleotides, wherein the oligonucleotides are attached to the array and wherein the oligonucleotides are complementary to the universal sequence.

4. The method of claim 1, further comprising contacting the array of nucleic acid templates with a conformationally labeled exonuclease, wherein the conformationally labeled exonuclease comprises a finger domain labeled with a second fluorescent label and a thumb domain labeled with a third label, wherein the second fluorescent label and third label are FRET pairs and wherein the FRET pairs are different from the FRET pairs of the conformationally labeled polymerase or wherein the third label is a quencher; under conditions wherein the conformationally labeled exonuclease catalyze sequential removal of nucleotide species from the nucleic acid templates, wherein the sequential removal of each different nucleotide species produces a conformational signal change from each of the conformationally labeled exonuclease and wherein the rate or time duration for the conformational signal change is distinguishable for at least one different nucleotide species that is removed;
    detecting a series of changes in the signal from the conformationally labeled exonuclease under the conditions and at the individual locations of the array; and
    determining the rates or time durations for the changes in the signal for the series of changes in the signal from the conformationally labeled exonuclease.

5. The method of claim 4, wherein the rate or time duration for the conformational signal change is distinguishable for only one of four different nucleotide species that are removed.

6. The method of claim 4, wherein the rates or time durations for the conformational signal change are distinguishable for four of four different nucleotide species that are removed.

7. The method of claim 4, wherein the at least one different nucleotide species that is removed comprises a modified alpha-phosphate moiety.

8. The method of claim 7, wherein the modified alpha-phosphate moiety comprises a moiety other than oxygen covalently attached to the alpha phosphate.

9. The method of claim 1, wherein the at least one non-natural nucleotide analog comprise at least four non-natural nucleotide analogs.

10. The method of claim 1, wherein the conformational signal change comprises increased FRET, decreased FRET, increased fluorescence quenching or decreased fluorescence quenching.

11. The method of claim 1, wherein the nucleic acid templates are individually resolved from each other.

12. The method of claim 1, wherein the nucleic acid templates are present in colonies and individual colonies comprise a plurality of templates that are the same species.

13. The method of claim 12, wherein the method comprises determining a sequence of nucleotides for a plurality of templates.

14. The method of claim 12, wherein the at least one non-natural nucleotide analog comprises a reversible terminator moiety.

15. The method of claim 1, wherein the at least one non-natural nucleotide analog comprise at least one caged nucleotide.

16. A method of determining nucleotide sequences, comprising
    (a) providing an array of different nucleic acid templates;
    (b) providing a mixture of nucleotide species, the mixture comprising (i) at least four different nucleotide species,
(ii) at least one of the four different nucleotide species comprising a reversible terminator moiety, and
(iii) at least two of the four different nucleotide species comprising an extendible 3' hydroxyl moiety;
(c) contacting the array of nucleic acid templates with a conformationally labeled polymerase, wherein the conformationally labeled polymerase comprises a finger domain labeled with a first fluorescent label and a thumb domain labeled with a second label, wherein the first fluorescent label and second label are FRET pairs or wherein the second label is a quencher; and the mixture of nucleotide species under conditions wherein the conformationally labeled polymerase catalyze sequential addition of the nucleotide species to form nucleic acid complements of the nucleic acid templates, wherein the sequential addition of each different nucleotide species produces a conformational signal change from the conformationally labeled polymerase,
wherein the rate or time duration for the conformational signal change is distinguishable for the at least two nucleotide species comprising the extendible 3' hydroxyl moiety, and
wherein a plurality of the nucleic acid complements incorporate the at least one nucleotide species that comprises the reversible terminator moiety;
(d) removing the reversible terminator moiety;
(e) detecting a series of changes in the signal from the conformationally labeled polymerase at individual locations of the array; and
(f) determining the sequence of nucleotides for the nucleic acid sample from the series of changes in the signal from the conformationally labeled polymerase.

17. The method of claim 16, wherein at least one of the four different nucleotide species is present at a substantially lower concentration than the concentration of any other nucleotide species in the mixture, whereby the nucleotide that is present at the substantially lower concentration produces a distinguishable rate or time duration for the conformational signal change.

18. The method of claim 16, further comprising repeating steps (c), (d) and (e) several times.

* * * * *